(12) United States Patent
Muniz et al.

(10) Patent No.: US 10,499,951 B2
(45) Date of Patent: Dec. 10, 2019

(54) EXTERNAL FIXATOR ASSEMBLY

(71) Applicant: GLOBUS MEDICAL, INC., Audubon, PA (US)

(72) Inventors: Sergio Muniz, Philadelphia, PA (US); David R. Jansen, Glenmoore, PA (US); Barclay Davis, Glenmoore, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 15/918,535

(22) Filed: Mar. 12, 2018

(65) Prior Publication Data

US 2018/0199962 A1 Jul. 19, 2018

Related U.S. Application Data

(63) Continuation of application No. 15/151,843, filed on May 11, 2016, now Pat. No. 9,943,337, which is a continuation-in-part of application No. 14/958,961, filed on Dec. 4, 2015, now Pat. No. 9,539,029, which is a continuation of application No. 14/957,793, filed on Dec. 3, 2015, now Pat. No. 9,872,707.

(51) Int. Cl.
*A61B 17/64* (2006.01)
*A61B 17/84* (2006.01)

(52) U.S. Cl.
CPC ...... *A61B 17/6466* (2013.01); *A61B 17/6425* (2013.01); *A61B 17/848* (2013.01)

(58) Field of Classification Search
CPC ............ A61B 17/6466; A61B 17/6425; A61B 17/848; A61B 17/645; A61B 17/60; A61B 17/6458; A61B 17/6483; A61B 17/7041; A61B 17/6416; A61B 17/8615; A61B 2017/606; F16B 2/10; F16B 7/0493; F16B 7/0433; Y10T 29/49826; Y10T 403/32; Y10T 403/7105; Y10T 403/32163; Y10T 403/32893; Y10T 403/71; Y10T 403/69; Y10T 403/7062; Y10T 403/581
USPC ...... 606/54–59, 324, 277; 403/72, 384, 385, 403/289; 411/433

See application file for complete search history.

(56) References Cited

U.S. PATENT DOCUMENTS

| | | |
|---|---|---|
| 4,244,360 A | 1/1981 | Dohogne |
| 4,299,520 A | 11/1981 | Iwata |
| 4,548,199 A | 10/1985 | Agee |
| 4,600,000 A | 7/1986 | Edwards |
| 4,600,344 A | 7/1986 | Sutenbach et al. |
| 4,628,919 A | 12/1986 | Clyburn |
| 4,684,284 A | 8/1987 | Bradley, Jr. |
| 4,828,444 A | 5/1989 | Oshida |
| 4,978,350 A | 12/1990 | Wagenknecht |

(Continued)

FOREIGN PATENT DOCUMENTS

| | | |
|---|---|---|
| WO | 9959490 A1 | 11/1999 |
| WO | 2005085658 A1 | 9/2005 |
| WO | 2016035053 A1 | 3/2016 |

*Primary Examiner* — Pedro Philogene

(57) ABSTRACT

External fixator assemblies, systems, and methods thereof. An external fixator system may include a plurality of fixator assemblies configured to connect a plurality of pins, for example, positioned on opposite sides of a fractured bone, with one more rods. The fixator assemblies may include a plurality of clamp assemblies which are configured to rotate relative to one another when the fixator assembly is in an unlocked position.

20 Claims, 21 Drawing Sheets

(56) References Cited

U.S. PATENT DOCUMENTS

| | | |
|---|---|---|
| 4,990,044 A | 2/1991 | Kimak |
| 5,591,164 A | 1/1997 | Nazre et al. |
| 5,630,815 A | 5/1997 | Pohl et al. |
| 5,662,650 A | 9/1997 | Bailey et al. |
| 5,752,954 A | 5/1998 | Mata et al. |
| 5,770,255 A | 6/1998 | Burrell et al. |
| 5,906,464 A | 5/1999 | Wedenig |
| 6,080,153 A | 6/2000 | Mata et al. |
| 6,565,564 B2 | 5/2003 | Hoffman et al. |
| 6,663,634 B2 | 12/2003 | Ahrens et al. |
| 6,702,814 B2 | 3/2004 | Walulik et al. |
| 6,942,664 B1 | 9/2005 | Voor et al. |
| 7,004,943 B2 | 2/2006 | Ferrante et al. |
| 7,041,103 B2 | 5/2006 | Hoffmann-Clair et al. |
| 7,179,038 B2 | 2/2007 | Reindl |
| 7,338,242 B2 | 3/2008 | Ellis et al. |
| 7,491,008 B2 | 2/2009 | Thomke et al. |
| 7,527,626 B2 | 5/2009 | Lutz et al. |
| 7,608,074 B2 | 10/2009 | Austin et al. |
| 7,618,417 B2 | 11/2009 | Thomke et al. |
| 7,699,848 B2 | 4/2010 | Hoffman et al. |
| 7,717,916 B2 | 5/2010 | Hajianpour |
| 7,722,609 B2 | 5/2010 | Bordeaux |
| 7,758,582 B2 | 7/2010 | Ferrante et al. |
| 7,806,623 B2 | 10/2010 | Thomke et al. |
| 7,875,030 B2 | 1/2011 | Hoffman-Clair et al. |
| 8,029,505 B2 | 10/2011 | Hearn et al. |
| 8,057,473 B2 | 11/2011 | Orsak et al. |
| 8,070,785 B2 | 12/2011 | Biscup |
| 8,100,971 B2 | 1/2012 | Trieu |
| 8,123,747 B2 | 2/2012 | Hajianpour |
| 8,147,490 B2 | 4/2012 | Bauer |
| 8,231,318 B2 | 7/2012 | Pitsch et al. |
| 8,372,073 B2 | 2/2013 | Hoffman et al. |
| 8,382,804 B2 | 2/2013 | Thomke et al. |
| 8,403,928 B2 | 3/2013 | Bordeaux |
| 8,523,858 B2 * | 9/2013 | Lessig ............... A61B 17/645 24/135 R |
| 8,540,713 B2 | 9/2013 | Zandona et al. |
| 8,585,702 B2 | 11/2013 | Orsak et al. |
| 8,628,530 B2 | 1/2014 | Hajianpour |
| 8,657,819 B2 | 2/2014 | Murner et al. |
| 8,685,023 B2 | 4/2014 | Dorawa et al. |
| 8,808,289 B2 | 8/2014 | Busch et al. |
| 8,827,997 B2 * | 9/2014 | Cremer ............... A61B 17/6466 606/59 |
| 8,945,129 B2 | 2/2015 | Dominik et al. |
| 8,998,902 B2 | 4/2015 | Hoffman et al. |
| 9,050,135 B2 | 6/2015 | Dominik et al. |
| 9,066,757 B2 | 6/2015 | Tan et al. |
| 9,084,632 B2 | 7/2015 | Orsak et al. |
| 9,155,562 B2 | 10/2015 | Cremer et al. |
| 9,188,147 B2 * | 11/2015 | Smith ............... F16B 33/02 |
| 9,273,715 B2 | 3/2016 | Bordeaux |
| 9,301,782 B2 | 4/2016 | Myers et al. |
| 9,539,029 B1 * | 1/2017 | Muniz ............... A61B 17/6425 |
| 9,872,707 B2 * | 1/2018 | Muniz ............... A61B 17/6425 |
| 9,943,337 B2 * | 4/2018 | Muniz ............... A61B 17/6466 |
| 2002/0077629 A1 | 6/2002 | Hoffman et al. |
| 2005/0245939 A1 | 11/2005 | Ferrante et al. |
| 2006/0255521 A1 | 11/2006 | Brunner et al. |
| 2009/0297294 A1 | 12/2009 | Li et al. |
| 2009/0299368 A1 | 12/2009 | Bauer |
| 2010/0262143 A1 | 10/2010 | Bordeaux |
| 2011/0066151 A1 | 3/2011 | Muerner et al. |
| 2012/0209264 A1 | 8/2012 | Zandona et al. |
| 2013/0144289 A1 * | 6/2013 | Dorawa ............... A61B 17/60 606/54 |
| 2014/0018803 A1 | 1/2014 | Lessig et al. |
| 2014/0336649 A1 | 11/2014 | Dorawa et al. |
| 2014/0350558 A1 | 11/2014 | Triplett et al. |
| 2014/0364853 A1 | 12/2014 | Mullaney et al. |
| 2015/0209081 A1 | 7/2015 | Venturini |
| 2015/0320446 A1 | 11/2015 | Cremer et al. |
| 2016/0038184 A1 | 2/2016 | Erickson |
| 2016/0199098 A1 | 7/2016 | Slagle |
| 2016/0199099 A1 | 7/2016 | Myers et al. |
| 2016/0367291 A1 | 12/2016 | Erickson et al. |
| 2017/0156757 A1 | 6/2017 | Muniz et al. |

* cited by examiner

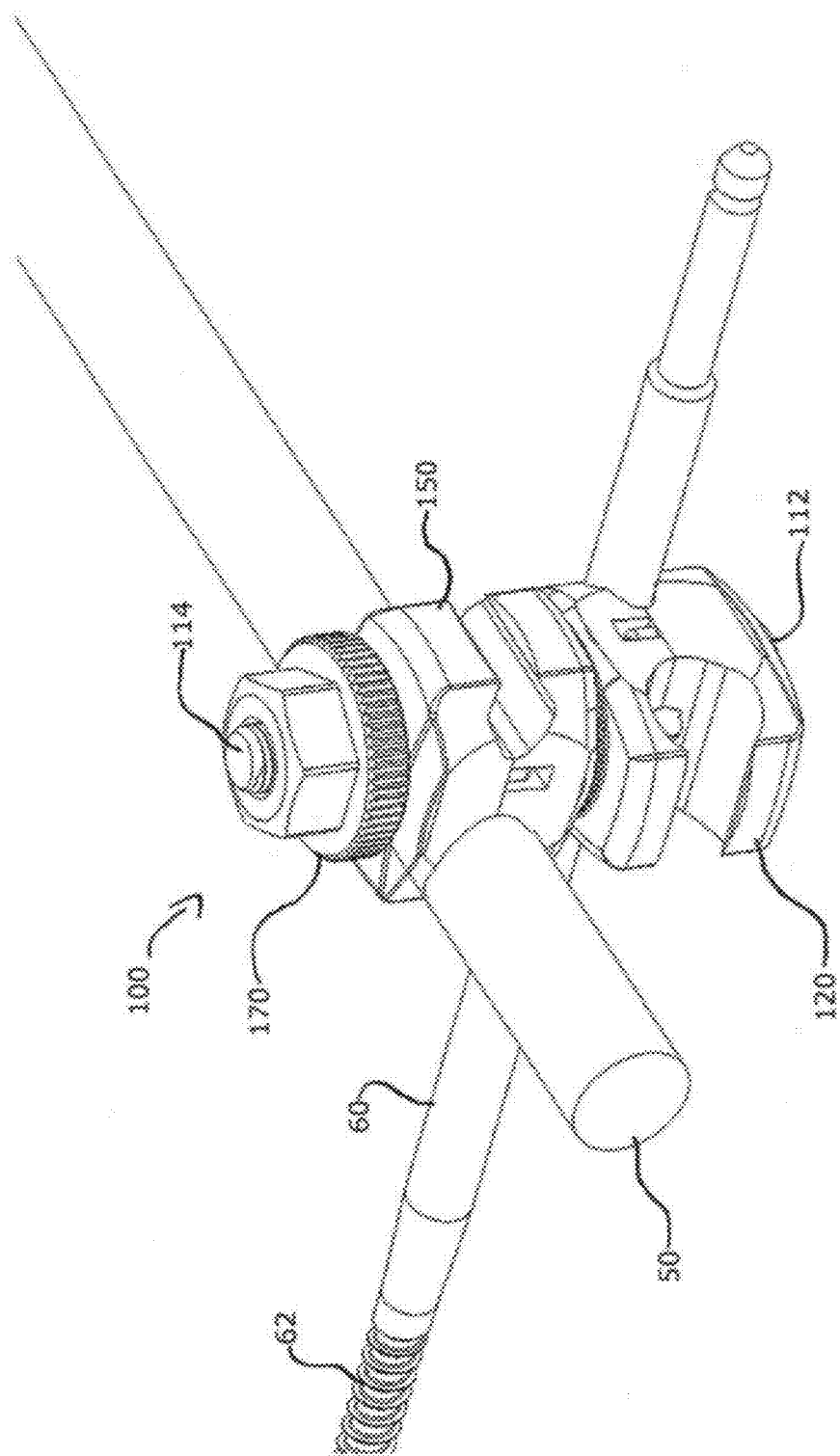

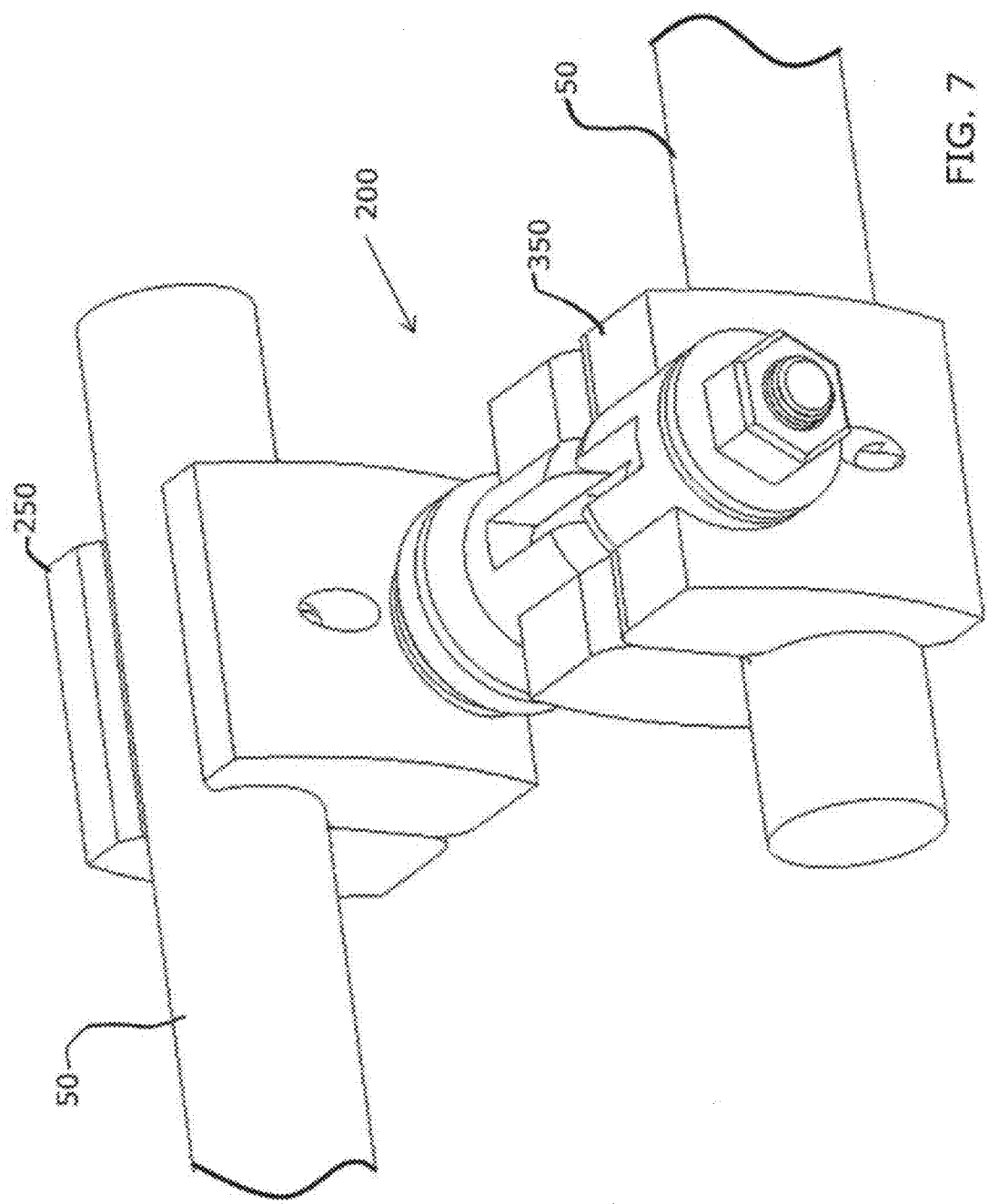

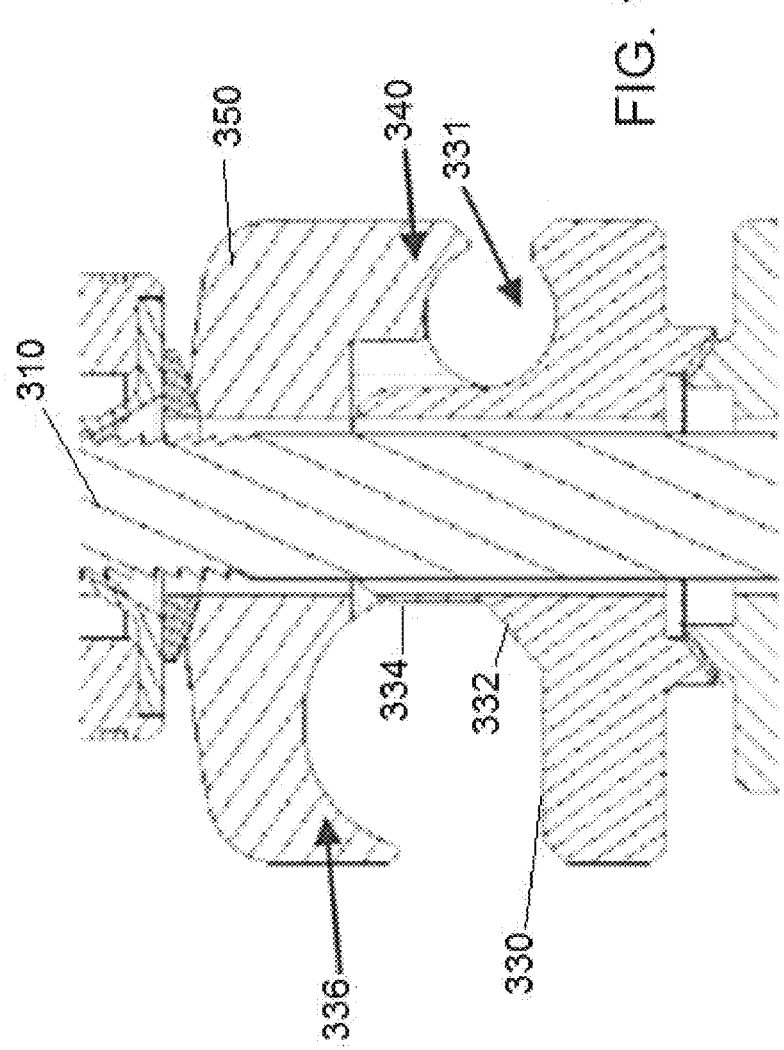

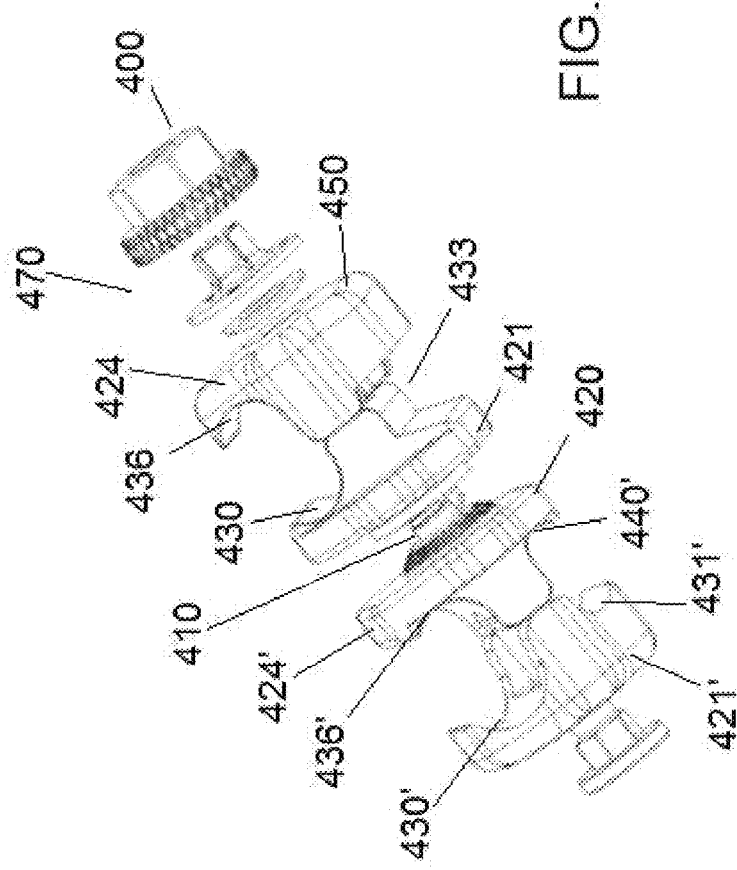

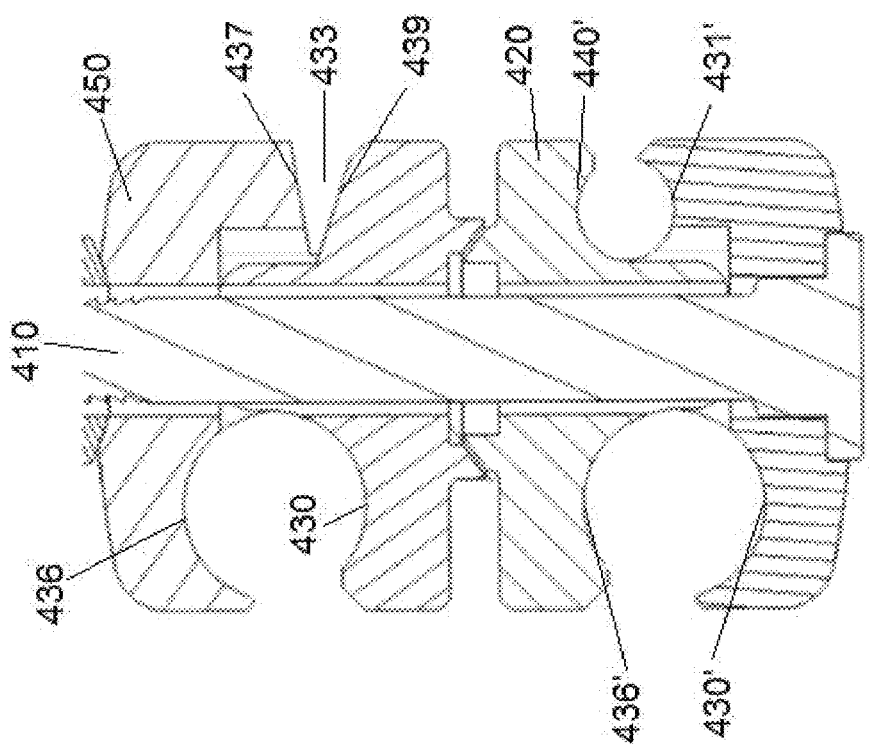

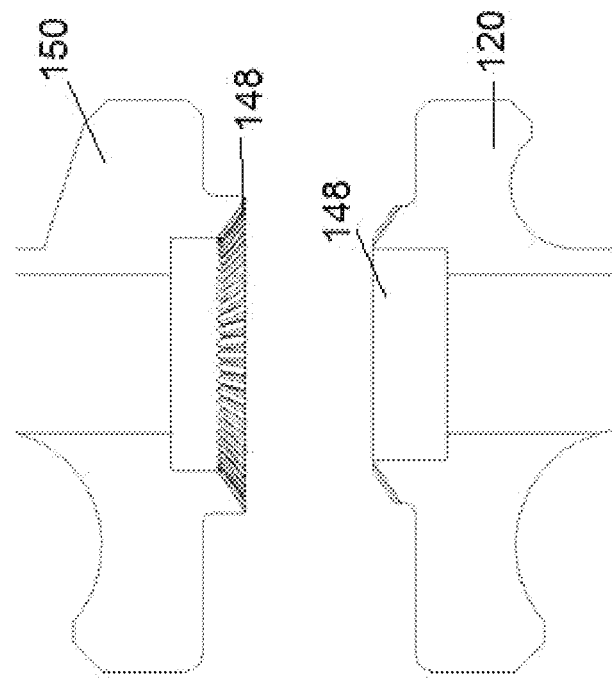
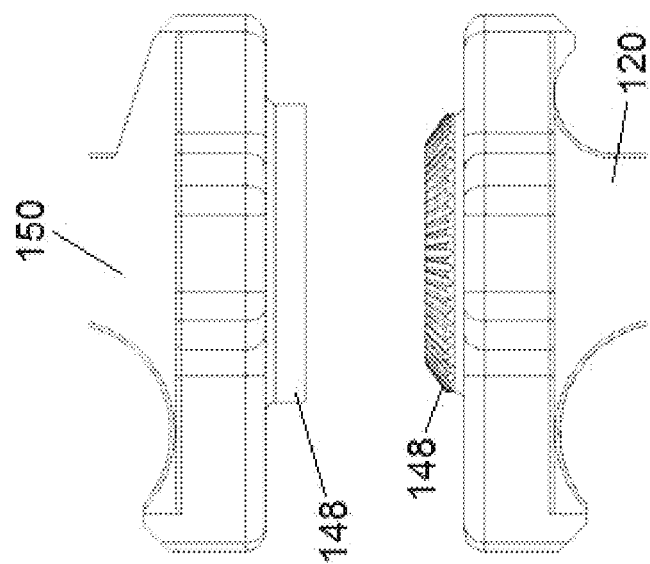

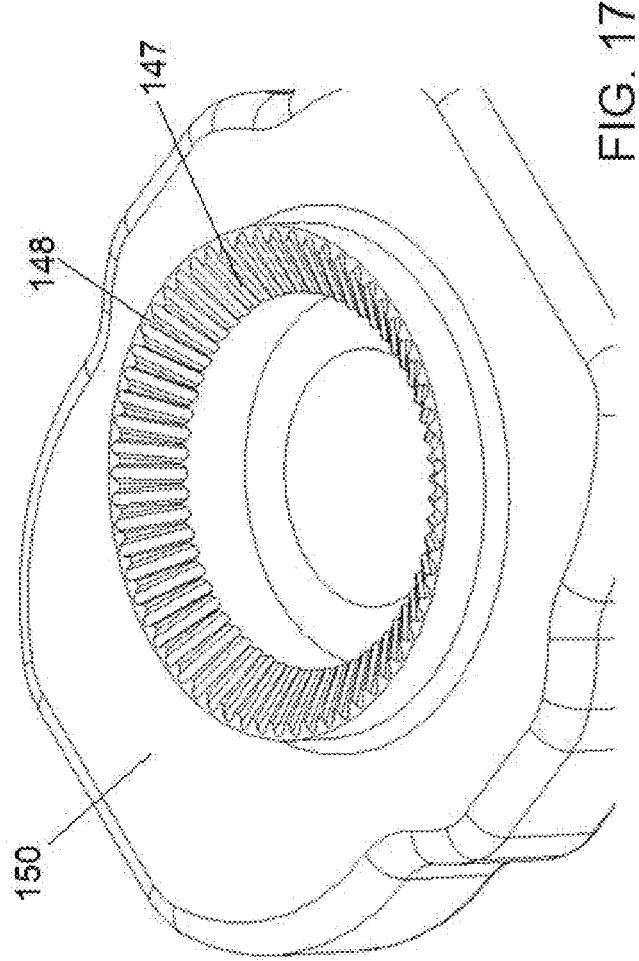

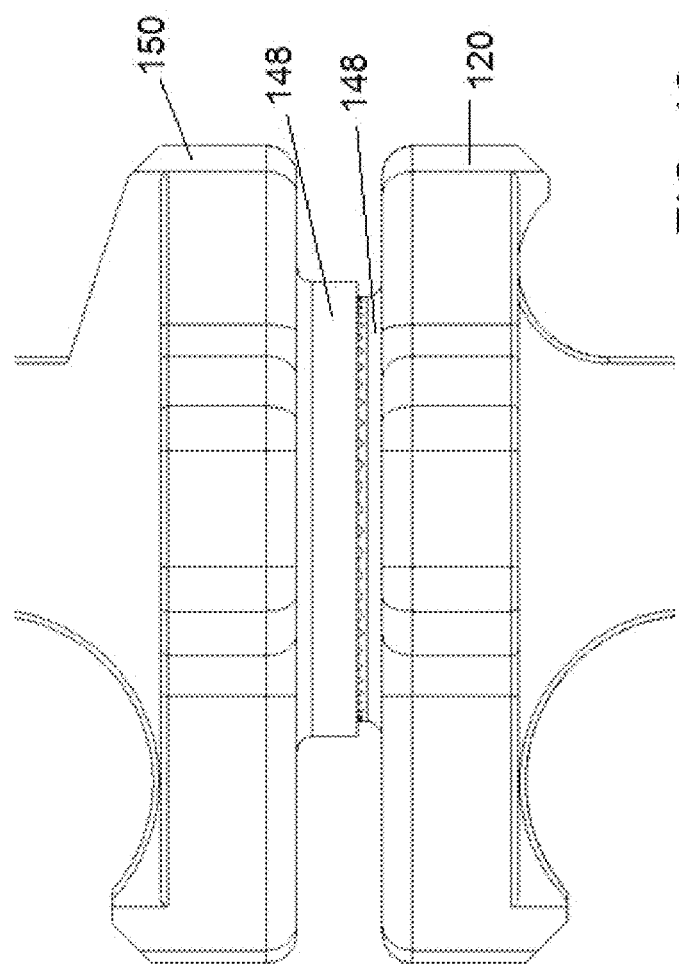

EXTERNAL FIXATOR ASSEMBLY

CROSS REFERENCE TO RELATED APPLICATIONS

The present application is a continuation of U.S. Ser. No. 15/151,843, filed May 11, 2016, which is a continuation-in-part application of U.S. Ser. No. 14/958,961, filed on Dec. 4, 2015, now U.S. Pat. No. 9,539,029, which is a continuation application of U.S. Ser. No. 14/957,793, filed Dec. 3, 2015, now U.S. Pat. No. 9,872,707, which are each incorporated herein by reference in their entireties for all purposes.

BACKGROUND

Field of the Invention

The present invention relates to external fixator assemblies, and, in particular, to external fixator assemblies having a plurality of clamps.

Description of the Related Art

External fixators have long been used in trauma incidents as a long-term care solution for reducing fractures and promoting bone healing. Recently, however, external fixators have been used for poly-traumatic patients as a way to stabilize fractures until a more definitive method of fixation can be determined and applied. The use of current external fixators to perform this temporary stabilization can be bulky and time-consuming.

Accordingly, there exists a need for lightweight, quick-assembly external fixators.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to one embodiment, an external fixator system may include a plurality of external fixator assemblies configured to connect a plurality of pins, for example, positioned on opposite sides of a fractured bone, with one more rods. The fixator assemblies may include a plurality of clamp assemblies which are configured to rotate relative to one another when the fixator assembly is in an unlocked position. Once the relative positioning of the pins and/or rods is achieved, for example, to stabilize the bone or bones, the fixator assemblies may be moved to a locked position, such that the clamp assemblies are fixed in position and no longer able to rotate relative to one another.

In one embodiment, the external fixator assembly includes a shaft having a distal end and a proximal end. The proximal end has at least one external thread. A plurality of clamp assemblies extends along the shaft from the distal end to the proximal end. A biasing member is disposed between adjacent of the plurality of clamp assemblies. A cap assembly is disposed over the proximal end of the shaft. The cap assembly is adapted to bias the plurality of clamp assemblies toward the distal end of the shaft.

In an alternative embodiment, the external fixator assembly includes a shaft comprising a distal end having a flange and a proximal end having at least one external thread. A clamp assembly is disposed along the shaft, proximal of the distal flange. A ratchet assembly biases the clamp assembly toward the distal flange. The ratchet assembly comprises a ratcheting buttress having a radially extending buttress flange and a hole extending through the flange. The hole is sized to allow the shaft to extend therethrough. A plurality of fingers extends proximally around the hole. Each of the plurality of fingers has a plurality of internal ratchet teeth adapted to engage the least one external thread on the proximal end on the shaft. A ratchet housing has a distal end having a radially extending housing flange adapted to engage the buttress flange and a proximal end having at least one internal thread adapted to threadably engage the at least one external thread on the shaft.

In still another alternative embodiment, the external fixator assembly includes a ratchet assembly. The ratchet assembly comprises a ratcheting buttress and a ratchet housing. The ratcheting flange having an annular flange having a buttress axial hole formed therein, a tang extending outwardly from the annular flange in a first direction, and a plurality of fingers extending outwardly from the annular flange in the first direction. The plurality of fingers surrounds the hole. Each of the plurality of fingers includes a plurality of internal ratchet teeth. The ratchet housing has an annular flange having a housing axial hole formed therein and a body attached to the flange. The annular flange has an external contoured surface, a first radially extending cavity adapted to receive the annular flange of the wrenching buttress, and an axially extending slot adapted to receive the tang. The body has a plurality of external flat surfaces extending around an outer perimeter thereof, a second radially extending cavity adapted to receive the plurality of fingers, and an internally threaded passage adjacent to the second radially extending cavity.

In yet another alternative embodiment, the external fixator assembly comprises a first shaft having a first coupling end and a first free end, a second shaft having a second coupling end and a second free end, and a coupling pivotally retaining the first coupling end and the second coupling end. A first clamp assembly is disposed on the first shaft between the coupling and the first free end. The first clamp assembly comprises a first inner clamp member disposed proximate to the coupling. The first inner clamp member has a first inner slot. A first outer clamp member is disposed proximate to the first free end. The first outer clamp member has a first outer slot. A first biasing member is disposed in the first inner slot and the first outer slot such that first biasing member biases the first inner clamp member toward the first outer clamp member. A second clamp assembly is disposed on the second shaft between the coupling and the second free end. The second clamp assembly comprises a second inner clamp member disposed proximate to the coupling. The second in the clamp member has a second inner slot. A second outer clamp is disposed proximate to the second free end. The second outer clamp member has a second outer slot. A second biasing member is disposed in the second inner slot and the second outer slot such that the second biasing member biases the second inner clamp member toward the second outer clamp member.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 2 is a perspective view of the external fixator assembly shown in FIG. 1 with a rod and a pin connected thereto;

FIG. 7 is a perspective view of the external fixator assembly shown in FIG. 6 with rods connected thereto;

FIG. 12 is a close-up view of a clamp assembly of the external fixator assembly of FIG. 11;

FIG. 13 is a top perspective view of an external fixator assembly according to a fourth exemplary embodiment being used to fixate adjacent bones;

FIG. 14 is a close-up view of a pair of clamp assemblies of the external fixator assembly of FIG. 13;

FIG. 15 is a front view of an interface between a first clamp assembly and a second clamp assembly in accordance with some embodiments;

FIG. 16 shows a cross-sectional view of the first clamp assembly and the second clamp assembly of FIG. 15;

FIG. 17 is a close-up view of teeth of a toothed locking half in accordance with some embodiments;

FIG. 18 is a close-up view of a first clamp assembly and a second clamp assembly in a fully tightened construct in accordance with some embodiments;

FIG. 20 is a side view of a pin in accordance with some embodiments.

DETAILED DESCRIPTION

Figure 1:
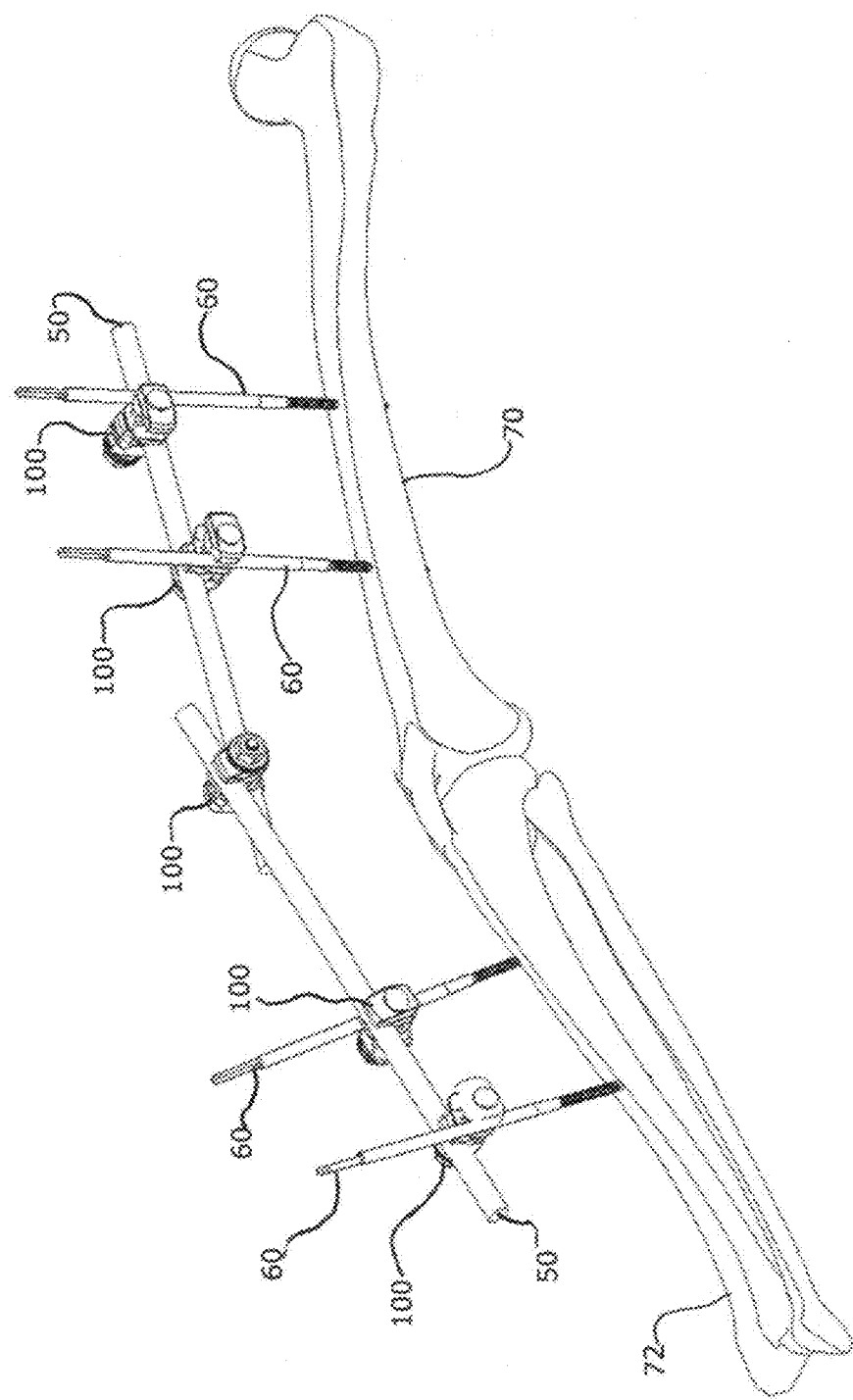
FIG. 1 is a perspective view of an external fixator assembly according to a first exemplary embodiment being used to fixate adjacent bones.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Also for purposes of this description, the terms "couple," "coupling," "coupled," "connect," "connecting," or "connected" refer to any manner known in the art or later developed of joining or connecting two or more elements directly or indirectly to one another, and the interposition of one or more additional elements is contemplated, although not required. Conversely, the terms "directly coupled," "directly connected," etc., imply the absence of such additional elements.

The present disclosure provides embodiments of external fixators that can be used to secure bone fractures. The inventive external fixators provide connections that enable a surgeon to rapidly and securely stabilize the fracture.

According to one embodiment, an external fixator system may include a plurality of external fixator assemblies configured to connect a plurality of pins, for example, positioned on opposite sides of a fractured bone, with one more rods. Each fixator assembly may include a plurality of clamp assemblies which are configured to rotate relative to one another when the fixator assembly is in an unlocked position. Once the relative positioning of the pins and/or rods is achieved, for example, to stabilize the fractured bone or bones, the fixator assemblies may be moved to a locked position, such that the clamp assemblies are fixed in position, thereby stabilizing the fracture.

Figure 1A:
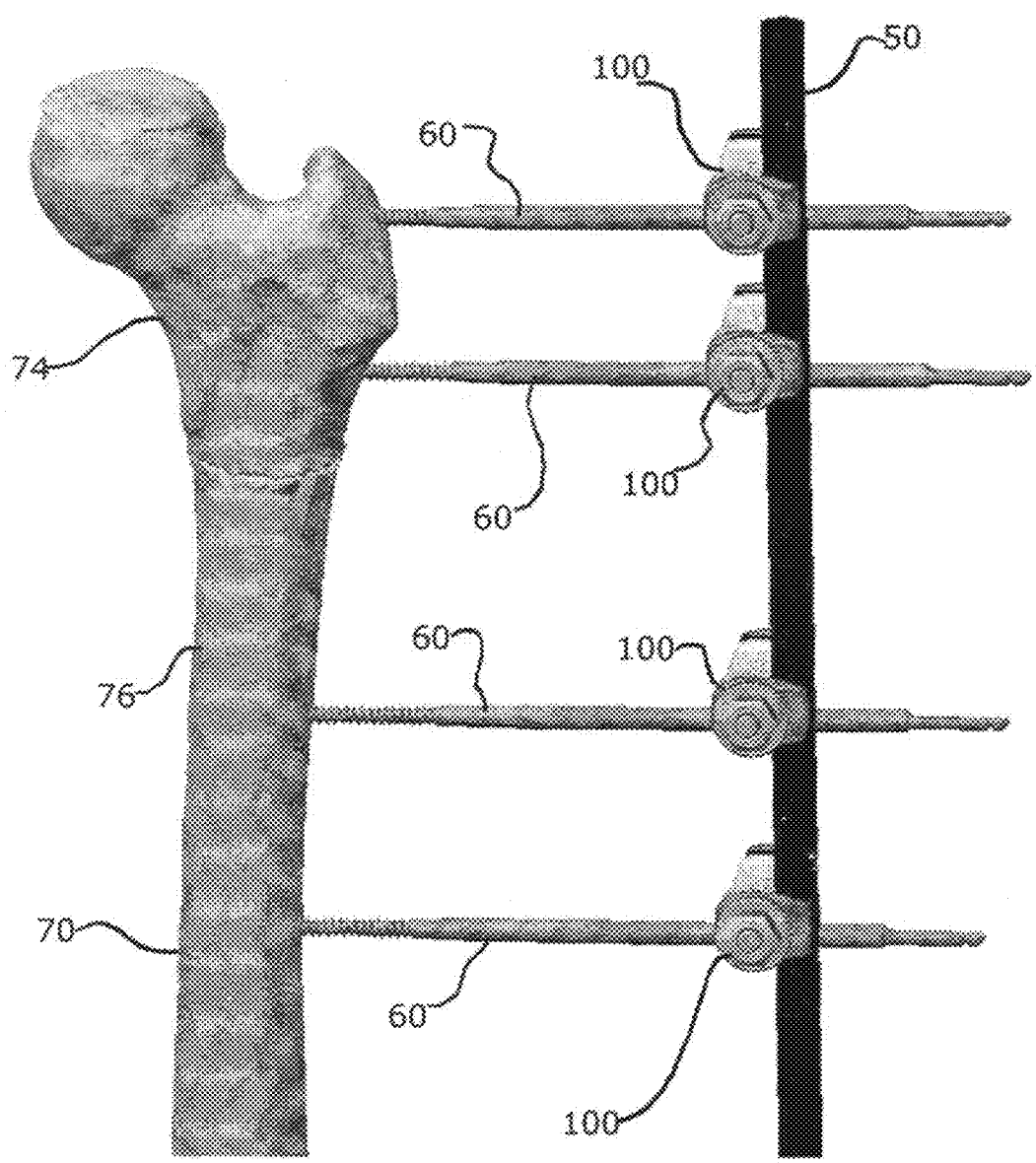
FIG. 1A is a perspective view of the external fixator assembly shown in FIG. 1 being used to fixate broken pieces of the same bone.

Referring to FIGS. 1-5, an external fixator assembly 100 ("fixator assembly 100") according to a first exemplary embodiment is shown. As shown specifically in FIGS. 1 and 1A, fixator assembly 100 is used in conjunction with rods 50 and pins 60 to secure and stabilize adjacent bones 70, 72 (shown in FIG. 1) or to stabilize broken pieces 74, 76 of the same bone 70 (shown in FIG. 1A). While a femur 70 and a tibia 72 are shown in FIG. 1, and femur 70 is shown in FIG. 1A, those skilled in the art will recognize that fixator assembly 100, along with rods 50 and pins 60, can be used to fixate other bones, and other bone pairs as well. Examples of bones may include, but are not limited to, the femur, tibia, fibula, humerus, radius, ulna, and phalanges. Although specific configurations of the external fixator systems are exemplified herein, it will be appreciated that the number, type, and location of rods 50, pins 60, and fixator assemblies 100 can be modified or changed based on the type and location of the bone, fracture, surgeon preference, and the like.

As shown in FIG. 2, fixator assembly 100 can be used to releasably secure rod 50 and pin 60 through the use of a plurality of connector assemblies. In an exemplary embodiment, rod 50 can be constructed from a rigid material, such as, for example, a carbon fiber, and can optionally be coated with a material, such as, for example, titanium, to make rod 50 more compatible with MRI use. It is contemplated that the rod 50 may be formed of any suitable material having suitable properties for this application. Rod 50 has a first diameter. The length of rod 50 can be varied depending on the need for a particular application.

Pin 60 can include a bone-engaging end, such as a self-tapping end 62, that is inserted into bone 70, 72. The pin 60 may also be constructed from any suitable biocompatible material. Optionally, end 62 can be coated with an antimicrobial material, such as, for example, silver or silver ions, in order to reduce the likelihood of infection. Pin 60 has a second diameter, smaller than the first diameter of rod 50. The length and diameter of pin 60 can vary, depending on the patient or the injury, as well as surgeon preference.

While FIGS. 1A and 2 show fixator assembly 100 being used to secure a single rod 50 and a single pin 60, those skilled in the art will recognize that fixator assembly 100 can, depending upon the particular situation and injury, be used to connect two rods 50, as shown in FIG. 1, or even two pins 60 (not shown).

Figure 4:
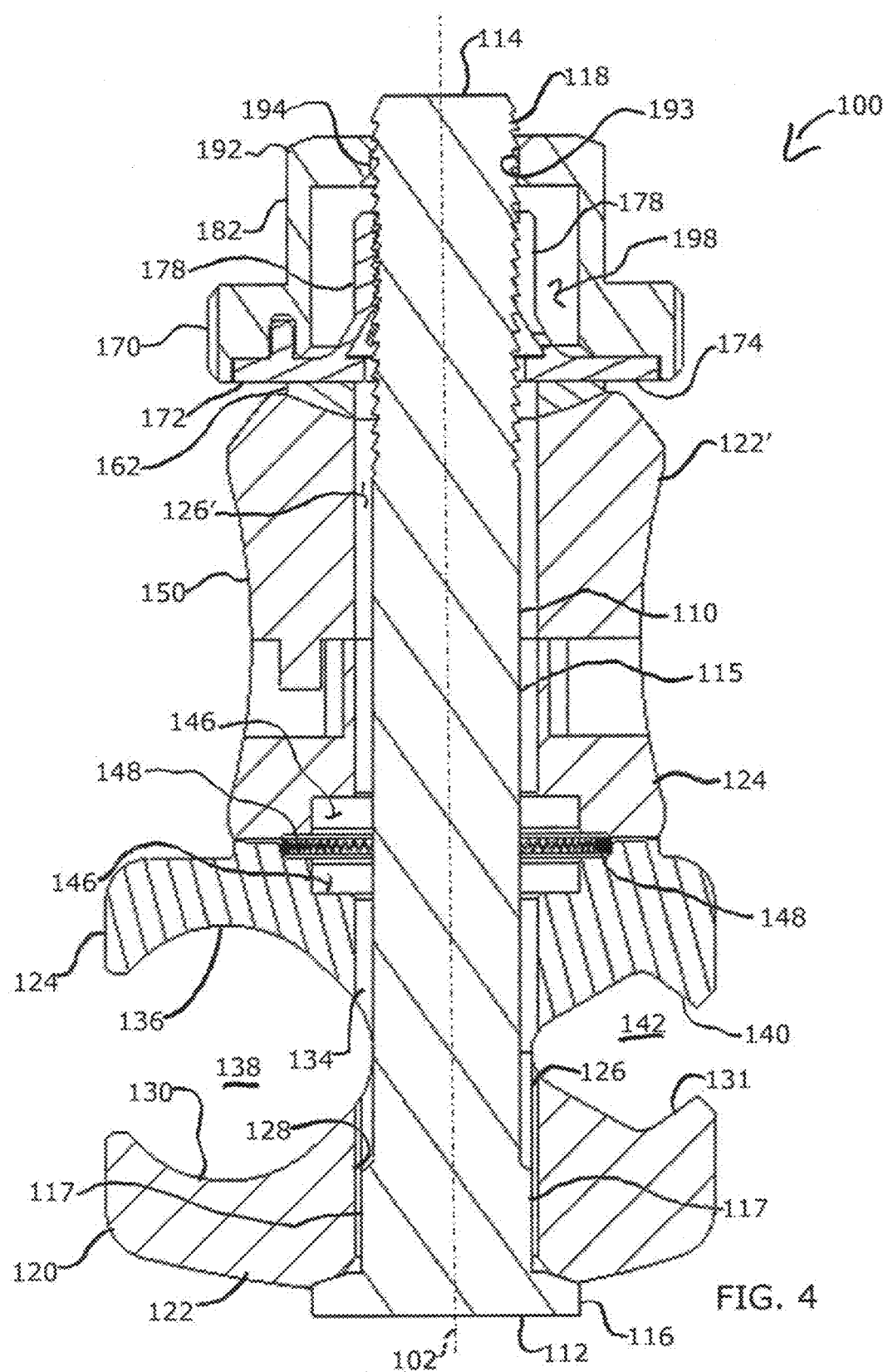
FIG. 4 is a side elevational view, in section, of the external fixator assembly shown in FIG. 1.

As shown in FIG. 4, fixator assembly 100 includes a longitudinal axis 102 extending therethrough. As used herein, the terms "longitudinal", "longitudinally", "axial", and "axially" refer to directions along the length of longitudinal axis 102 or to directions extending parallel to longitudinal axis 102. Further, the terms "radial" and "radially" refer to directions extending perpendicular to or extending outwardly from longitudinal axis 102.

Figure 3:
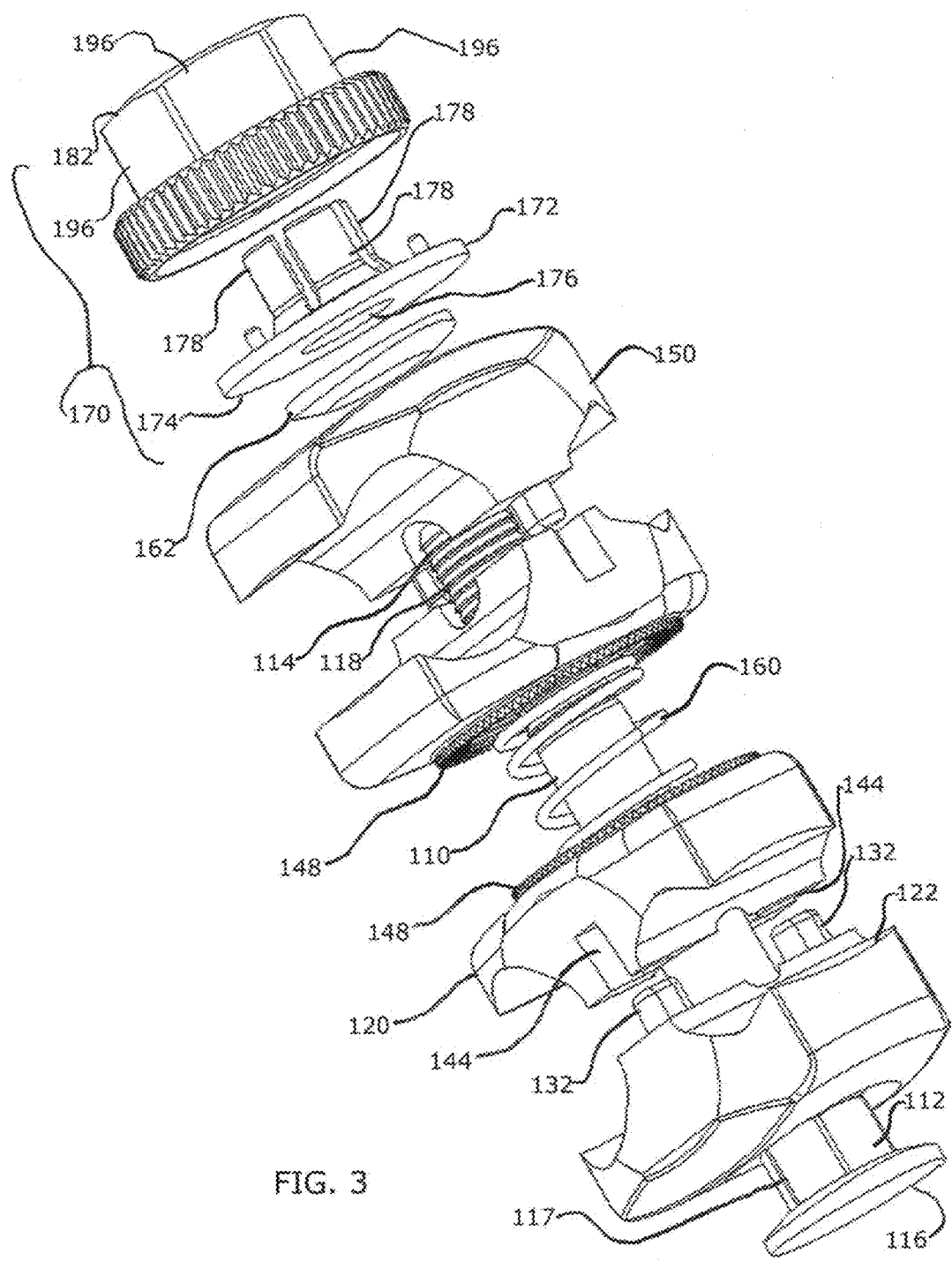
FIG. 3 is an exploded perspective view of the external fixator assembly shown in FIG. 1.

Referring now to FIGS. 2 and 3, fixator assembly 100 includes a shaft 110 and a plurality of clamp assemblies 120, 150 extending along shaft 110. Shaft 110 extends along longitudinal axis 102. A biasing member 160 is disposed between adjacent of the plurality of clamp assemblies 120, 150. A cap, or ratchet, assembly 170 secures clamp assemblies 120, 150 onto shaft 110.

Shaft 110 has a distal end 112 and a proximal end 114 extending away from distal and 112. As used herein with respect to fixator assembly 100, the term "distal" refers to a direction toward the bottom of the page of FIG. 4, and the term "proximal" refers to a direction toward the top of the page of FIG. 4.

Distal end 112 includes a radially extending flange 116 and at least one flat surface 117 extending proximally of flange 116. While FIG. 4 shows two flat surfaces 117, those skilled in the art will recognize that shaft 110 can include more or less than two flat surfaces 117.

Proximal end 114 of shaft 110 has at least one external thread 118. Optionally, a length of shaft 115 between distal end 112 and proximal end 114 can be generally circular, that is, devoid of any flat surfaces or threads. Shaft 110 is sufficiently long to allow for the insertion of clamp assemblies 120, 150 and ratchet assembly 170 thereon.

Clamp assemblies 120, 150 extend along shaft 110 from distal end 112 toward proximal end 114 such that clamp assembly 120 engages flange 116 and clamp assembly 150 engages clamp assembly 120. While two clamp assemblies 120, 150 are shown, those skilled in the art will recognize that more than two clamp assemblies 120, 150 can be used with fixator assembly 100. Alternatively, it can be envisioned that only a single clamp assembly 120 is used with fixator assembly 100.

Clamp assemblies 120, 150 may be, although not necessarily, identical to each other. Clamp assembly 120 includes a lower member 122 and an upper member 124 extending proximally of lower member 122. Lower member 122 includes an axially extending passage 126 that is sized to allow shaft 110 to extend therethrough. Passage 126 can include internal flat surfaces 128 that are adapted to engage with flat surfaces 117 on shaft 110 to prevent lower member 122 of clamp assembly 120 from rotating with respect to shaft 110.

Lower member 122 includes a first generally U-shaped portion 130 having a radius that is sized to receive a portion of rod 50. Lower member 122 also includes a second generally U-shaped portion 131, radially disposed away from first concave portion 130, having a radius that is sized to receive a portion of pin 60. As shown in FIG. 3, lower member 122 also includes a plurality of tangs 132 extending outwardly therefrom in a proximal direction toward upper member 124.

Upper member 124 includes an axially extending passage 134 that is sized to allow shaft 110 to extend therethrough. Upper member 136 further includes a first generally inverted U-shaped portion 136 having a radius that is sized to receive a portion of rod 50, such that, when upper member 124 is biased toward lower member 122, rod 50 is received in a cavity 138 formed by first generally U-shaped portion 130 of lower member 122 and first generally inverted U-shaped portion 136 of upper member 124.

Upper member 124 also includes a second generally inverted U-shaped portion 140, radially disposed away from first generally inverted U-shaped portion 136, having a radius that is sized to receive a portion of pin 60, such that, when upper member 124 is biased toward lower member 122, pin 60 is received in a cavity 142 formed by second generally inverted U-shaped portion 131 of lower member 122 and second generally inverted U-shaped 140 of upper member 124.

As shown in FIG. 3, upper member 124 also includes a plurality of slots 144 formed therein, such that each slot 144 is adapted to releasably receive a tang 132 from lower member 122, thereby preventing upper member 124 from rotating about longitudinal axis 102 relative to lower member 122. Upper member 124 also includes a spring cavity 146 that is sized to receive biasing member 160. A toothed locking half 148 surrounds spring cavity 146.

Clamp assembly 150 is similar to clamp assembly 120 with the exception that, instead of internal flat surfaces 128, clamp assembly 150 includes a member 122' having an axially extending passage 126' sufficiently larger than the diameter of shaft 110 such that clamp assembly 150 is freely rotatable about shaft 110 and is also rotatable relative to clamp assembly 120. As shown in FIGS. 3 and 4, clamp assembly 150 is inserted over shaft 110 "upside down" relative to clamp 120 such that toothed locking half 148 of clamp assembly 150 is engageable with toothed locking half 148 of clamp assembly 120 such that, when clamp assembly 150 is biased against clamp assembly 120, toothed locking half 148 of clamp assembly 150 engages toothed locking half 148 of clamp assembly 120, preventing rotation of clamp assembly 150 with respect to clamp assembly 120.

Each toothed locking half 148 includes a plurality of teeth or the like. In an exemplary embodiment, each toothed locking half 148 includes about 90 teeth, such that clamp assembly 150 can be indexed with respect to clamp assembly 120 about 4°. Those skilled in the art, however, will recognize that each toothed locking half 148 can include more or less than 90 teeth, such that the amount indexing of clamp assembly 150 with respect clamp assembly 120 is adjustable accordingly.

As shown in FIG. 3, biasing member 160 is disposed between clamp assembly 120 and clamp assembly 150 and is retained between clamp assembly 120 and clamp assembly 150 within spring cavities 146. In an exemplary embodiment, biasing member 160 is a helical spring, although those skilled in the art will recognize that other types of biasing members can be used. Biasing member 160 biases clamp assembly 120 and clamp assembly 150 apart from each other, such that clamp assembly 120 and clamp assembly 150 securely engage rod 50 that may be inserted into cavity 138 and/or pin 160 that may be inserted into cavity 142.

Figure 5:
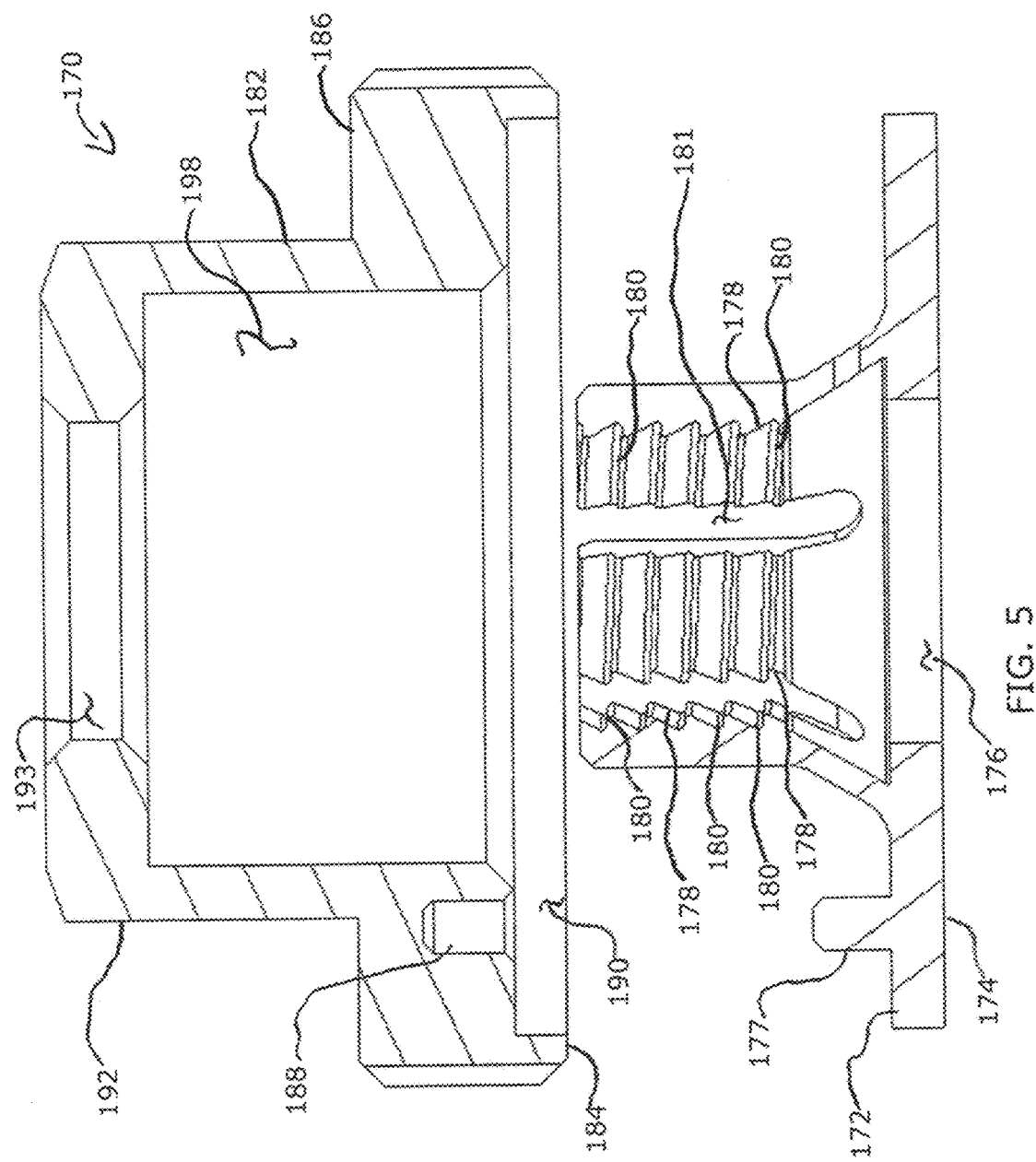
FIG. 5 is an exploded sectional view of a ratchet assembly used with the external fixator assembly shown in FIG. 1.

Referring to FIGS. 3-5, ratchet assembly 170 is disposed over proximal end 114 of shaft 110, such that ratchet assembly 170 biases clamp assemblies 120, 150 toward distal end 112 of shaft 110 and flange 116 so that clamp assemblies 120, 150 are not rotatable with respect to each other. A washer 162 is axially disposed between second clamp assembly 150 and ratchet assembly 170 to distribute compressive forces applied by ratchet assembly 170 onto clamp assembly 150.

Ratchet assembly 170 comprises includes a ratcheting buttress 172 that is adapted to translate axially along shaft 110 from proximal end 114 toward distal end 112. Ratcheting buttress 172 comprises a radially extending annular flange 174 having an axially extending hole 176 therein. Hole 176 is sized to allow shaft 112 to extend therethrough. A tang 177 extends longitudinally outwardly from flange 174.

A plurality of fingers 178 extend proximally around hole 176. Each of the plurality of fingers 178 has a plurality of longitudinally spaced internal ratchet teeth 180 adapted to engage external thread 118 on proximal end 114 of shaft 110. A gap 181 extends between each of adjacent fingers 178 to allow fingers 178 to bias away from longitudinal axis 102, thereby allowing thread 118 to ratchet along ratchet teeth 180 when ratchet assembly 170 is pressed onto shaft 110.

A ratchet housing 182 is disposed over ratcheting buttress 172. Ratchet housing 182 includes a distal end 184 having a radially extending housing flange 186 that is adapted to engage buttress flange 174. Flange 186 includes a slot 188 that is adapted to receive tang 177 from flange 174 such that, when tang 177 is inserted into slot 188, ratchet housing 182 is not rotatable relative to ratcheting buttress 172.

An exterior surface of housing flange 186 includes a contoured surface, such as, for example, a knurled surface, that provides a gripping surface for the user to be able to manually rotate ratchet housing 182 about shaft 110. An interior of housing flange 186 includes a first radially extending cavity 190 adapted to receive annular flange 174 of ratchet buttress 172.

Ratchet housing 182 further includes a proximal body 192 having an internally threaded passage 193 with at least one internal thread 194 adapted to threadably engage external thread 118 on shaft 110. Body 192 further comprises a plurality of flat surfaces 196 extending around a perimeter thereof. Flat surfaces 196 allow for the application of a tool, such as, for example, a wrench or other torquing device (not shown) to tighten fixator assembly 100 in order to secure rod(s) 50 and/or pin(s) 60. Body 192 also includes a second radially extending cavity 198 that is adapted to receive the plurality of fingers 178. As shown in FIG. 4, cavity 198 is sufficiently large to allow fingers 178 to bias away from shaft 110 to allow ratcheting buttress 172 to be slid distally along shaft 110.

To assemble fixator assembly 100, first clamp assembly 120 is slid from proximal end 114 of shaft 110 to distal end 112 shaft 110, bottoming out on flange 116. First clamp assembly 120 is aligned such that toothed locking half 148 is facing proximal end 114 of shaft 100. Next, biasing member 160 is slid along shaft 110 such that at least a portion of biasing member 160 is seated within spring cavity 146.

Second clamp assembly 150 is then slid from proximal end 114 of shaft 110, toward first clamp assembly 120. Second clamp assembly 150 is aligned such that toothed locking half 148 is facing distal end 112 of shaft 100 so that at least a remaining portion of biasing member 160 is seated within spring cavity 146 in second clamp assembly 150 and so that toothed locking half 148 of second clamp assembly 150 is facing toothed locking half 148 of first clamp assembly 120.

Washer 162 is slid over shaft 110. Ratchet assembly 170 is then slid over shaft 110 so that internal thread 194 engages external threads 118 on shaft 110. At this point, cavities 138, 142 are sufficiently large to allow rod 50 be slid into cavity 138 and pin 60 to be slid into cavity 142 and also to allow second clamp assembly 150 to axially rotate relative to first clamp assembly 120.

In this condition, the surgeon can align rod 50 and pin 60 in desired positions with respect to fixator assembly 100. The surgeon can then provisionally tighten ratchet assembly 170 by further sliding ratchet assembly 170 distally along shaft 110 and then perform a final tightening of fixator assembly 100 by applying a wrench or other court applying device (not shown) to flat surfaces 196 on ratchet housing 182 and rotating ratchet housing 182 relative to shaft 110.

Ratchet assembly 170 allows for the rapid application of clamp assemblies 120, 150 onto bar 50 and/or pin 60. Ratchet assembly 170 also provides a quick method for provisional tightening of fixator assembly 100 while the surgeon is assembling fixator assembly 100 with bar(s) 50 and pin(s) 60. Once set, a final tightening of ratchet assembly 170 can be applied using a torque limiting adapter, for example, under power.

According to one embodiment, a method of installing the external fixator system, for example, at the site of one or more broken bones, may include inserting one or more pins 60 into the afflicted bone (for example, on opposite sides of the fracture); attaching one or more fixator assemblies 100 to each pin 60; and securing the one or more pins 60 to adjacent pins 60 by connecting one or more rods 50 between adjacent fixator assemblies 100. If the construct needs to be extended, for example, to bridge multiple bones or multiple fractures, the same fixator assembly 100 can also be used to connect two or more rods 50 together.

Figure 6:
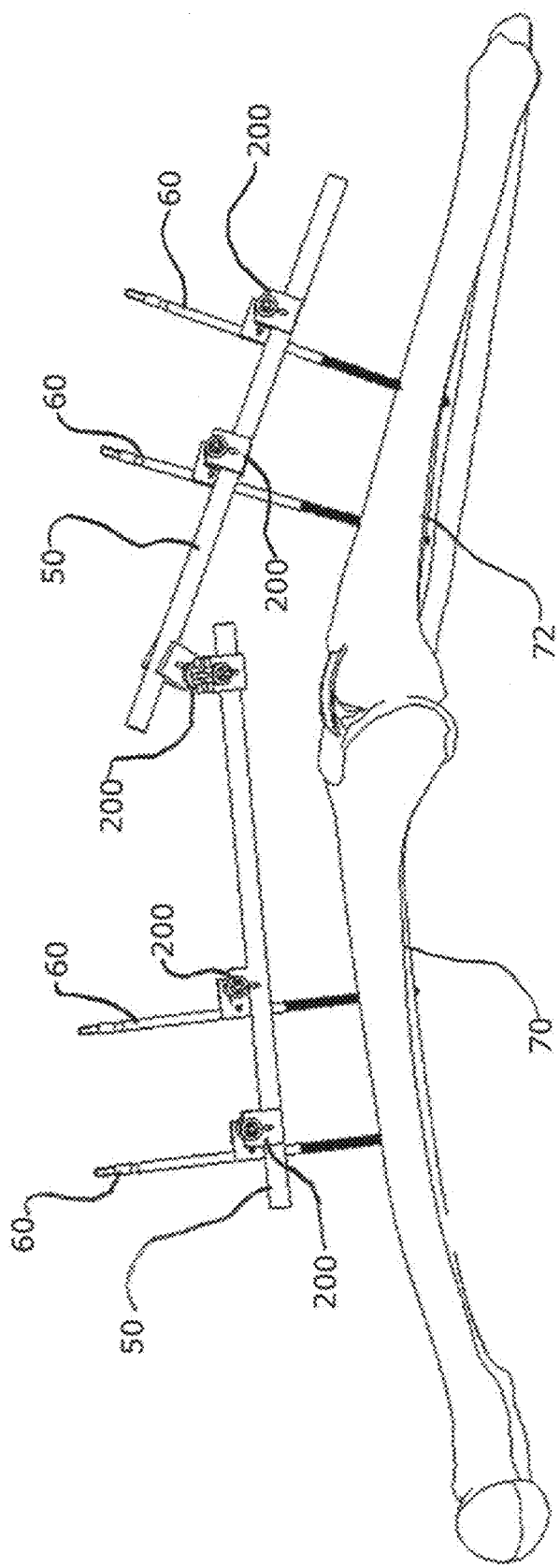
FIG. 6 is a perspective view of external fixator assembly according to a second exemplary embodiment being used to fixate adjacent bones.
Figure 7A:
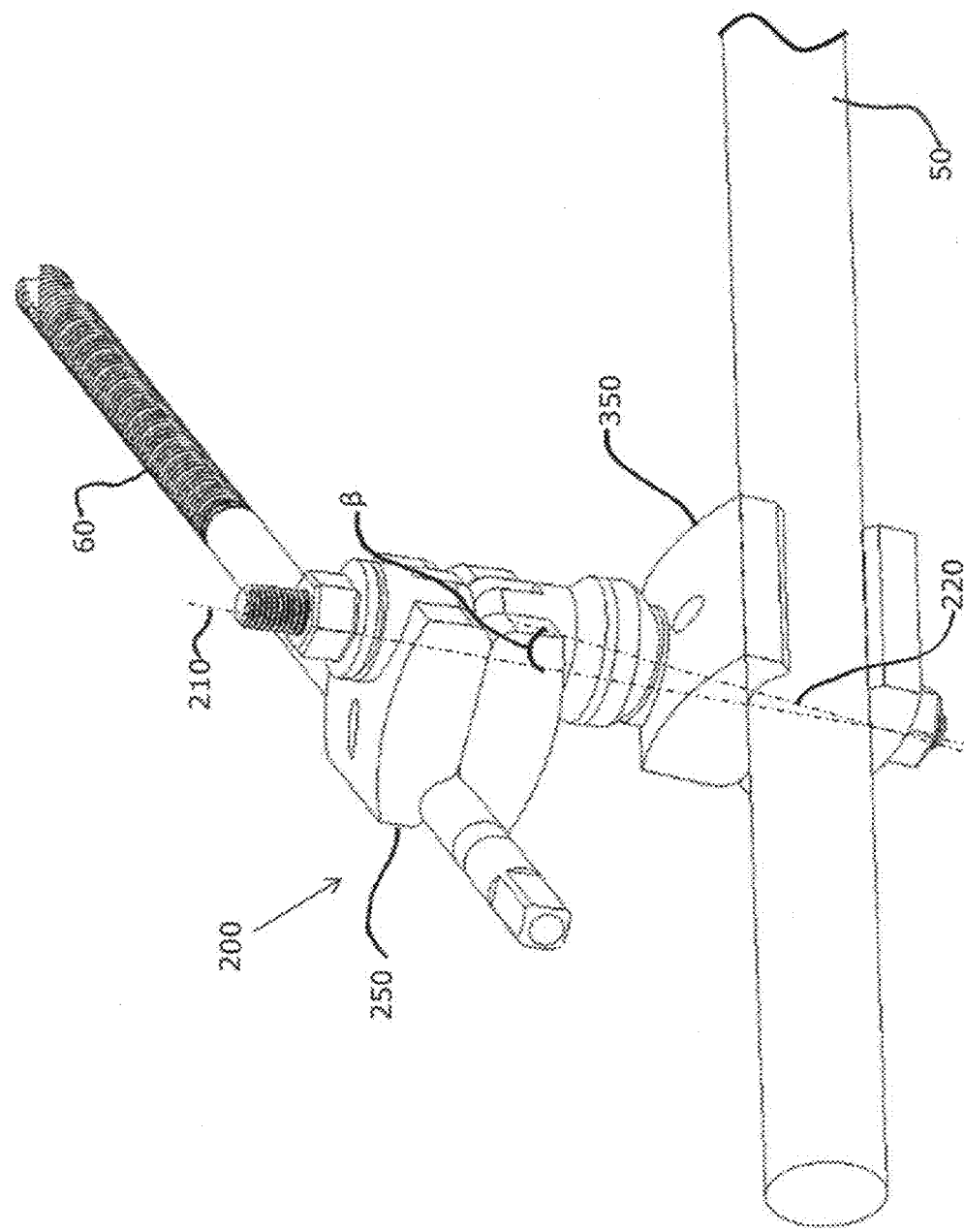
FIG. 7A is a perspective view of the external fixator assembly shown in FIG. 6 with a rod and a pin connected thereto.

An alternative embodiment of an external fixator assembly 200 ("fixator assembly 200") is shown in FIGS. 6-10. FIG. 6 shows fixator assembly 200 being used with both rods 50 and pins 60 to secure and stabilize adjacent bones 70, 72 in a patient. FIG. 7 shows fixator assembly 200 being used to secure two rods 50 in a generally parallel arrangement, while FIG. 7A shows fixator assembly 200 being used to secure a single rod 50 and a single pin 60 in a skewed arrangement.

Figure 8:
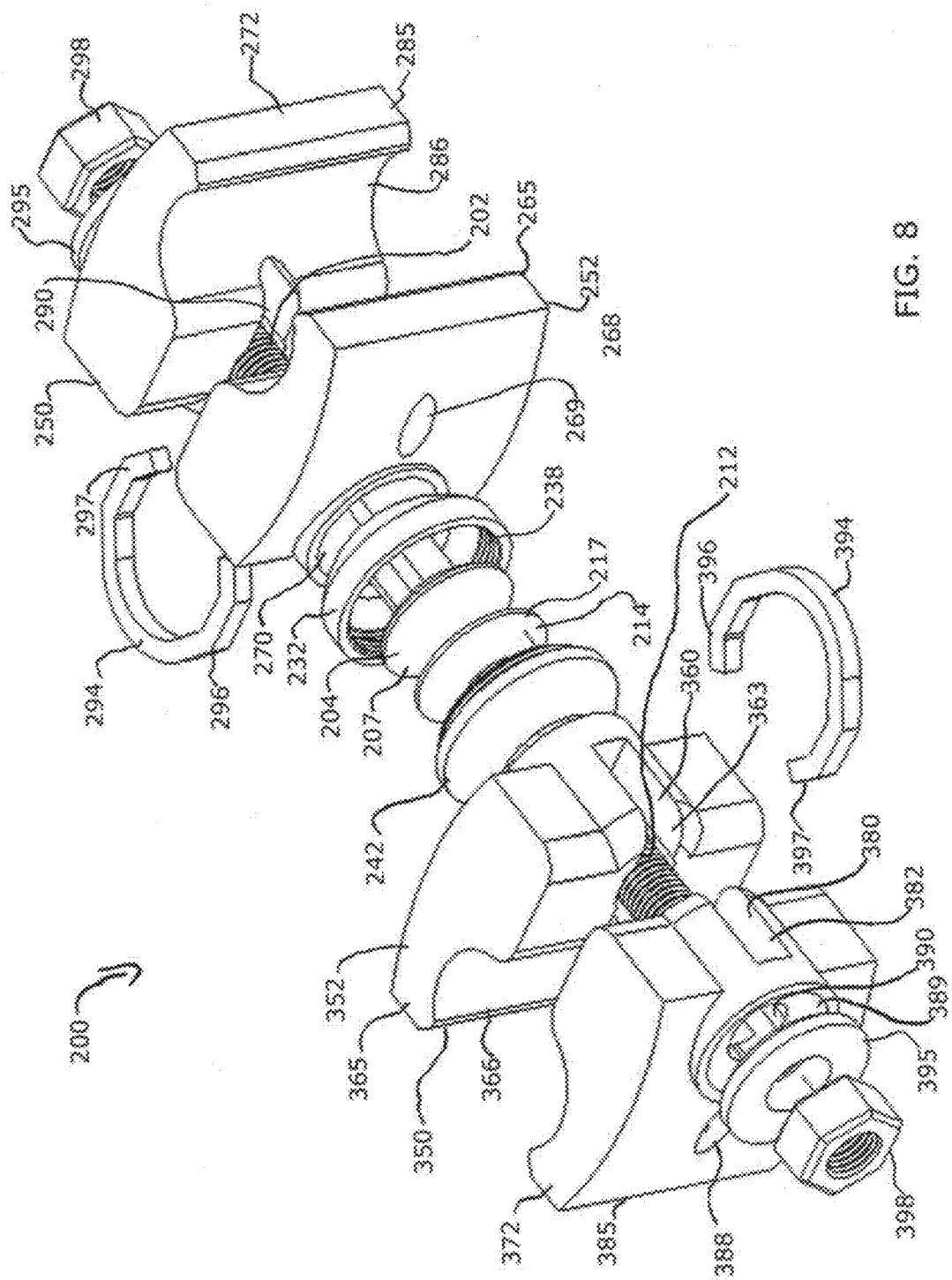
FIG. 8 is an exploded perspective view of the external fixator assembly shown in FIG. 6.
Figure 9:
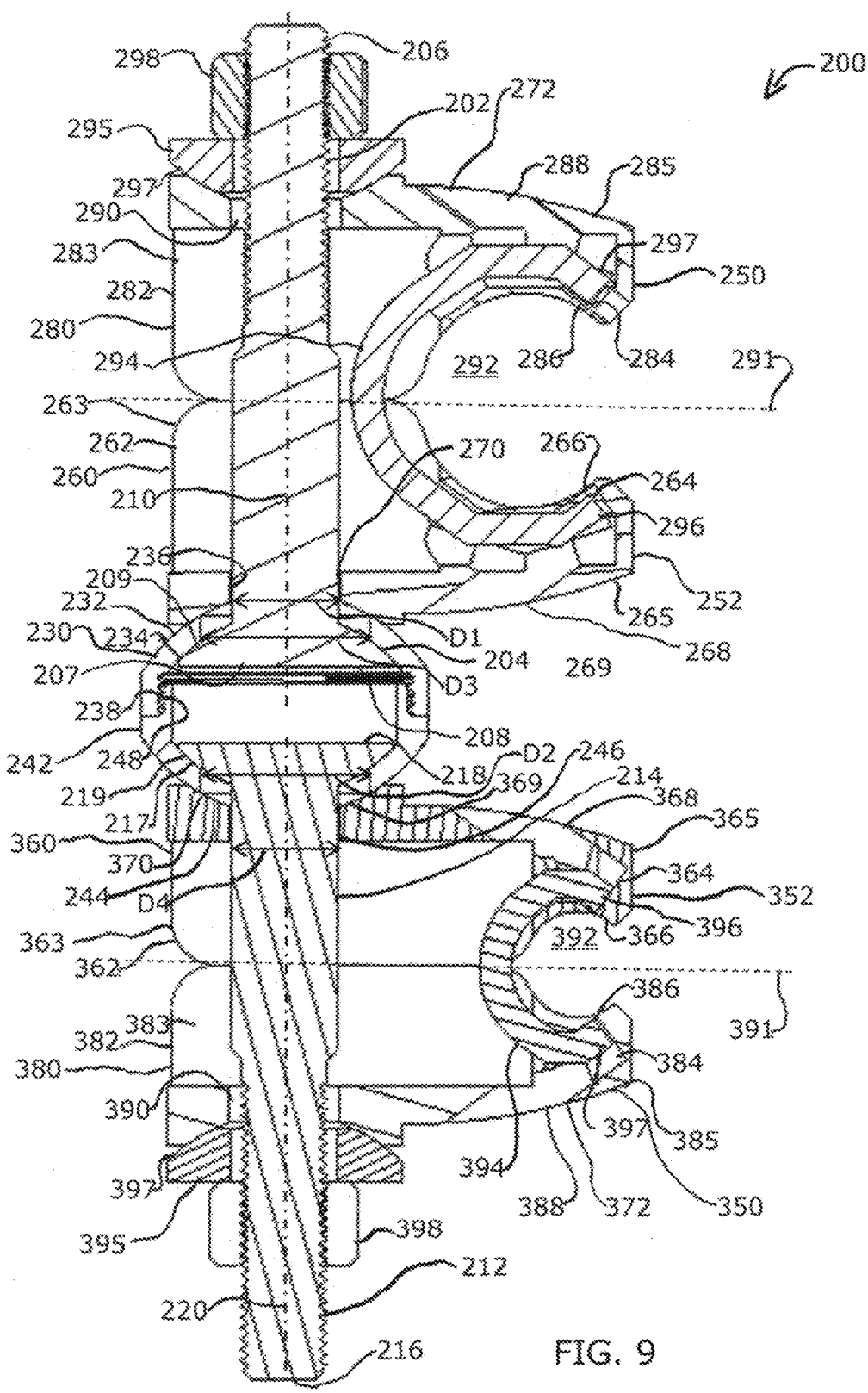
FIG. 9 is a side elevational view, in section, of the external fixator assembly shown in FIG. 6.

Referring to the exploded view of fixator assembly 200, shown in FIG. 8 and the sectional view shown in FIG. 9, a fixator assembly 200 includes a first shaft 202 having a first coupling end 204 and a first free end 206. First coupling end 204 has an outer diameter D1. First free end 206 has a narrower diameter than outer diameter D1. First coupling end 204 terminates in a first lip 207, having a generally flat face 208 and a generally convex outer face 209. A first longitudinal axis 210 extends along the length of first shaft 202.

Similarly, a second shaft 212 has a second coupling end 214 and a second free end 216. Second coupling end 214 has an outer diameter D2. Second free end 216 has a narrower diameter than outer diameter D2. Second coupling end 214 terminates in a second lip 217, having a generally flat face 218 and a generally convex outer face 219. A second longitudinal axis 220 extends along the length of second shaft 212.

A coupling 230 pivotally retains first coupling end 204 and second coupling end 214 therein. Coupling 230 includes a first cup, or clamshell portion 232 having a concave interface 234 that is contoured to receive generally convex outer face 209 of first coupling end 204. Additionally, first clamshell portion 232 includes an opening 236, having a diameter D3, such that outer diameter D1 of first coupling end 204 is smaller than the diameter D3, but first lip 207 is larger than the size of opening 236 such that, when first shaft 202 is inserted through opening 236, first lip 207 is retained within first clamshell portion 232.

Likewise, coupling 230 also includes a second cup, or clamshell portion 242 having a concave interface 244 that is contoured to receive generally convex outer face 219 of second coupling end 214. Additionally, second clamshell portion 242 includes an opening 246, having a diameter D4, such that outer diameter D2 of second coupling end 214 is smaller than the diameter D4, but second lip 217 is larger than the size of opening 246 such that, when second shaft 212 is inserted through opening 246, second lip 217 is retained within second clamshell portion 242.

In an exemplary embodiment, first clamshell portion 232 includes female threads 238 and second clamshell portion 242 includes matching male threads 248 such that first clamshell portion 232 can be threadedly connected to second clamshell portion 242. Optionally, to prevent first clamshell portion 232 from being separated from second clamshell portion 242, first clamshell portion 232 can be welded or otherwise permanently secured to second clamshell portion 242 at the connection of female threads 238 and male threads 248.

As used herein, the term "inner" is used to define a direction toward coupling 230, and the term "outer" is used to define a direction away from coupling 230. A first clamp assembly 250 is disposed on first shaft 202 between coupling 230 and first free end 206 of first shaft 202. First clamp assembly 250 includes a first inner clamp member 252 disposed proximate to coupling 230. First inner clamp member 252 has a first inner slot 260. First inner slot 260 has an open end 262, located at a shaft end 263, and a blind end 264, located at a finger end 265. Finger end 265 includes an arcuate cutout 266 that extends in an arc greater than 90°. A drill passage 268 extends obliquely through finger end 265 to allow for the formation of blind end 264.

First inner clamp member 252 also includes a concave surface 269 that engages concave interface 234 of first clamshell portion 232 so that first inner clamp member 252 is slidable along at least a portion of concave interface 234. Additionally, first inner clamp member 252 includes a through-opening 270 sized to allow first shaft 202 to pass therethrough. Through-opening 270 is sized such that a minimum clearance exists between through-opening 270 and first shaft 202.

First clamp assembly 250 further includes a first outer clamp member 272 disposed proximate to first free end 206. First outer clamp member 272 has a first outer slot 280. First outer slot 280 has an open end 282, located at shaft end 283, and a blind end 284, located at a finger end 285. Finger end 285 includes an arcuate cutout 286 that extends in an arc greater than 90°. A drill passage 288 extends obliquely through finger end 285 to allow for the formation of blind end 284. Similar to concave surface 269 in first inner clamp member 252, first outer clamp member 272 also includes a concave surface 289. Additionally, first outer clamp member 272 includes a through-opening 290 sized to allow free end 206 of first shaft 202 to pass therethrough.

In an exemplary embodiment, first outer clamp member 272 is generally a mirror image of first inner clamp member 252 across a transverse axis 291. When first inner clamp member 252 and first outer clamp member 272 are assembled on shaft 202, as shown in FIG. 9, a retaining cavity 292 is formed between finger end 265 and finger end 285. Retaining cavity 292 has a wall portion that extends an arc of greater than 180°. In an exemplary embodiment, retaining cavity 292 is sized to allow the insertion of rod 50 therein.

A first biasing member 294 is disposed in first inner slot 260 and first outer slot 280. In an exemplary embodiment, first biasing member 294 is a C-shaped spring having a first end 296 that is inserted into blind end 264 of first inner slot 260 and a second end 297 that is inserted into blind end 284 of first outer slot 280 such that first biasing member 294 biases first inner clamp member 252 toward first outer clamp member 272.

A first washer 295 is disposed over first shaft 202 and against first outer clamp member 272. First washer 295 has a contoured inner surface 297 for engagement with concave surface 289. A nut 298 is threaded onto first shaft 202 to secure first clamp assembly 250 against coupling 230.

Similar to first clamp assembly 250, a second clamp assembly 350 is disposed on second shaft 212 between coupling 230 and second free end 216. Second clamp assembly 350 includes a second inner clamp member 352 disposed proximate to coupling 230. Second inner clamp member 352 has a second inner slot 360. Second inner slot 360 has an open end 362, located at a shaft end 363 and a blind end 364, located at a finger end 365. Finger end 365 includes an arcuate cutout 366 that extends in an arc greater than 90°. A drill passage 368 extends obliquely through finger end 365 to allow for the formation of blind end 364.

Second inner clamp member 352 also includes a concave surface 369 that engages concave interface 334 of second clamshell portion 242 so that second inner clamp member 352 is slidable along at least a portion of concave interface 334. Additionally, second inner clamp member 352 includes a through-opening 370 sized to allow second shaft 212 to pass therethrough. Through-opening 370 is sized such that a minimum clearance exists between through-opening 370 and second shaft 212.

Second clamp assembly 350 further includes a second outer clamp member 372 disposed proximate to second free end 216. Second outer clamp member 372 has a second outer slot 380. Second outer slot 380 has an open end 382, located at shaft end 383 and a blind end 384, located at a finger end 385. Finger end 385 includes an arcuate cutout 386 that extends in an arc greater than 90°. A drill passage 388 extends obliquely through finger end 385 to allow for the formation of blind end 384. Similar to concave surface 369 in second inner clamp member 352, second outer clamp member 372 also includes a concave surface 389. Additionally, second outer clamp member 372 includes a through-opening 390 sized to allow free end 216 of second shaft 212 to pass therethrough.

In an exemplary embodiment, second outer clamp member 372 is generally a mirror image of second inner clamp member 352 across a transverse axis 391. When second inner clamp member 352 and second outer clamp member 372 are assembled on shaft 212, as shown in FIG. 9, a retaining cavity 392 is formed between finger end 365 and finger end 385. Retaining cavity 392 has a wall portion that extends an arc of greater than 180°. In an exemplary embodiment, retaining cavity 392 is sized to allow the insertion of pin 60 therein.

A second biasing member 394 is disposed in second inner slot 360 and second outer slot 380. In an exemplary embodiment, second biasing member 394 is a C-shaped spring having a first end 396 that is inserted into blind end 364 of second inner slot 360 and a second end 397 that is inserted into blind end 384 of second outer slot 380 such that second biasing member 394 biases second inner clamp member 352 toward second outer clamp member 372.

A second washer 395 is disposed over second shaft 212 and against second outer clamp member 372. Second washer 395 has a contoured inner surface 397 for engagement with concave surface 389. A nut 398 is threaded onto second shaft 212 to secure second clamp assembly 350 against coupling 230.

To assemble fixator assembly 200, first shaft 202 is inserted into first clamshell portion 232, such that first lip 207 is seated in first clamshell portion 232 and second shaft 212 and second shaft 212 is inserted into second clamshell portion 242, such that second lip 217 is seated in second clamshell portion 242. First and second clamshell portion 232, 242 are then fixedly secured to each other.

First inner clamp member 252 and first outer clamp 272 are placed next to each other, such that first inner slot 260 and first outer slot 280 are aligned with each other, forming first clamp assembly 250. First biasing member 294 is then inserted through first inner slot 260 and first outer slot 280 such that first end 296 of first biasing member 294 is inserted into blind end 264 of first inner slot 260 and second end 297 of biasing member 294 is inserted into blind end 284 of first outer slot 280, thereby securing first inner clamp member 252 and first outer clamp member 272 to each other and providing a compressive force to bias finger end 265 of first inner clamp member 252 and finger end 285 of first outer clamp member 272 toward each other.

First clamp assembly 250 is then slid over first shaft 202 such that first shaft 202 extends through through-openings 270, 290 and first shaft 202 extends through first inner slot 260 and first outer slot 280 such that first shaft 202 retains first biasing member 294 in first inner slot 260 and first outer slot 280. Washer 295 is slid over first shaft 202 and nut 298 is then threaded onto first shaft 202 to secure first clamp assembly 250 against coupling 230.

Similarly, second inner clamp member 352 and second outer clamp 372 are placed next to each other, such that second inner slot 360 and second outer slot 380 are aligned with each other, forming second clamp assembly 350. Second biasing member 394 is then inserted through second inner slot 360 and second outer slot 380 such that first end 396 of second biasing member 394 is inserted into blind end 364 of second inner slot 360 and second end 397 of biasing member 394 is inserted into blind end 384 of second outer slot 380, thereby securing second inner clamp member 352 and second outer clamp member 372 to each other and providing a compressive force to bias finger end 365 of second inner clamp member 352 and finger end 385 of second outer clamp member 372 toward each other.

Second clamp assembly 350 is then slid over second shaft 212 such that second shaft 212 extends through through-openings 370, 390 and second shaft 212 extends through second inner slot 360 and second outer slot 280 such that second shaft 212 retains second biasing member 394 in second inner slot 360 and second outer slot 380. Washer 395 is slid over second shaft 212, and nut 398 is then threaded onto second shaft 212 to secure second clamp assembly 350 against coupling 230.

Rod 50 can be inserted into retaining cavity 292. Because retaining cavity 292 has a wall portion that defines an arc of greater than 180°, with rod 50 in retaining cavity 292, the compressive action of biasing member 294 and the tightening of nut 298 securely retain rod 50 within retaining cavity 292.

Similarly, pin 60 can be inserted into retaining cavity 392. Because retaining cavity 392 has a wall portion that defines an arc of greater than 180°, with pin 60 in retaining cavity 392, the compressive action of biasing member 394 and the tightening of nut 298 securely retain pin 60 within retaining cavity 392.

In order to rotate first clamp assembly 250 about first shaft 210, nut 298 can be loosened sufficiently to allow such rotation. The compressive action of first biasing member 294 retains rod 50 within retaining cavity 292 to allow such rotation, without adversely affecting the retention of rod 50 within first clamp assembly 250.

Likewise, in order to rotate second clamp assembly 350 about second shaft 220, nut 398 can be loosened sufficiently to allow such rotation. The compressive action of second biasing member 394 retains pin 60 within retaining cavity 392 to allow such rotation, without adversely affecting the retention of pin 60 within second clamp assembly 350.

Figure 10:
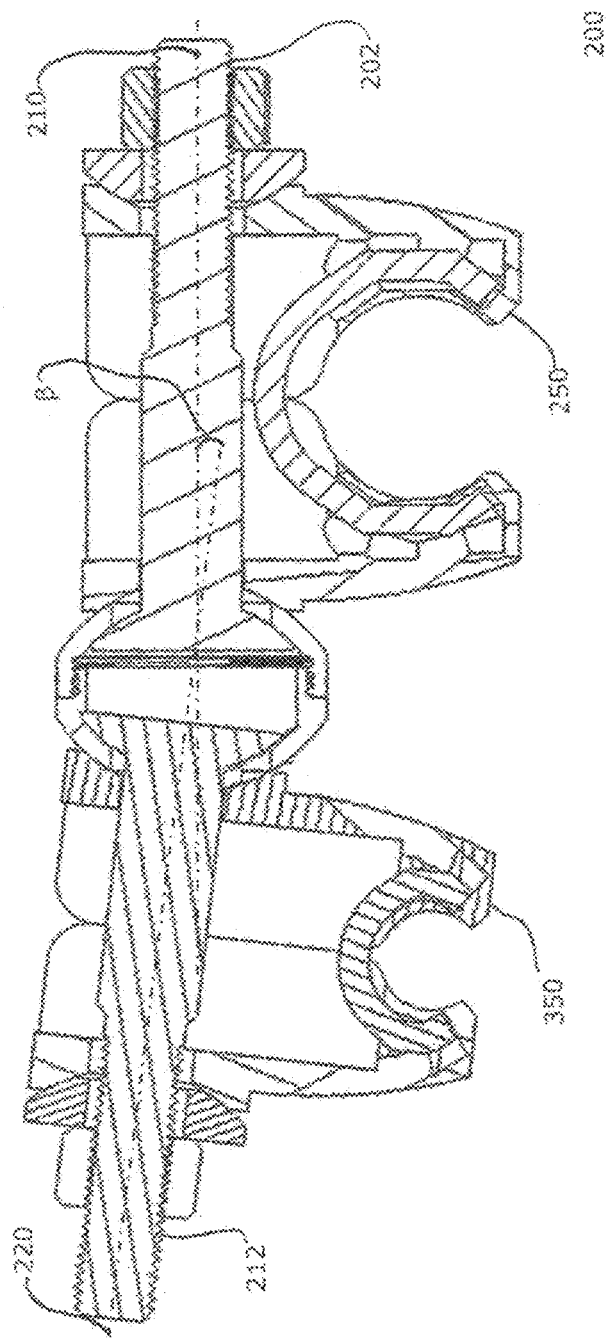
FIG. 10 is a side elevational view, in section, of the external fixator assembly shown in FIG. 9, with one shaft pivoted relative to the other shaft.

Additionally, because diameter D1 of first coupling end 204 is smaller than diameter D3 of opening 236 in first clamshell portion 232 and diameter D2 of second coupling end 214 is smaller than diameter D4 of opening 246 in second clamshell portion 242, first longitudinal axis 210 of first shaft 202 does not necessarily have to be collinear with second longitudinal axis 220 of second shaft 212. As shown in FIG. 10, first longitudinal axis 210 can extend at an oblique angle β relative to second longitudinal axis 220, allowing for first clamp assembly 250 to angularly pivot relative to second clamp assembly 350, thereby allowing for angular adjustment of first clamp assembly 250 relative to second clamp assembly 350. FIG. 7A shows an example of such angular adjustment.

According to one embodiment, a method of installing the external fixator system, for example, at the site of one or more broken bones, may include inserting a first pin 60 into the afflicted bone on one side of the fracture; inserting a second pin 60 on an opposite side of the fracture; attaching a first fixator assembly 200 to the first pin 60 and a second fixator assembly 200 to the second pin 60; articulating the first or second clamp assembly 250, 350 relative to the other of the first or second clamp assembly 250, 350 into a position for receiving the rod 50; connecting the rod 50 between the first and second fixator assemblies 200 in order to secure the first and second pins 60 together. If the construct needs to be extended, for example, to bridge multiple bones or multiple fractures, a third fixator assembly 200 may be articulated and positioned to secure and connect the rod 50 to an additional rod 50.

Figure 11:
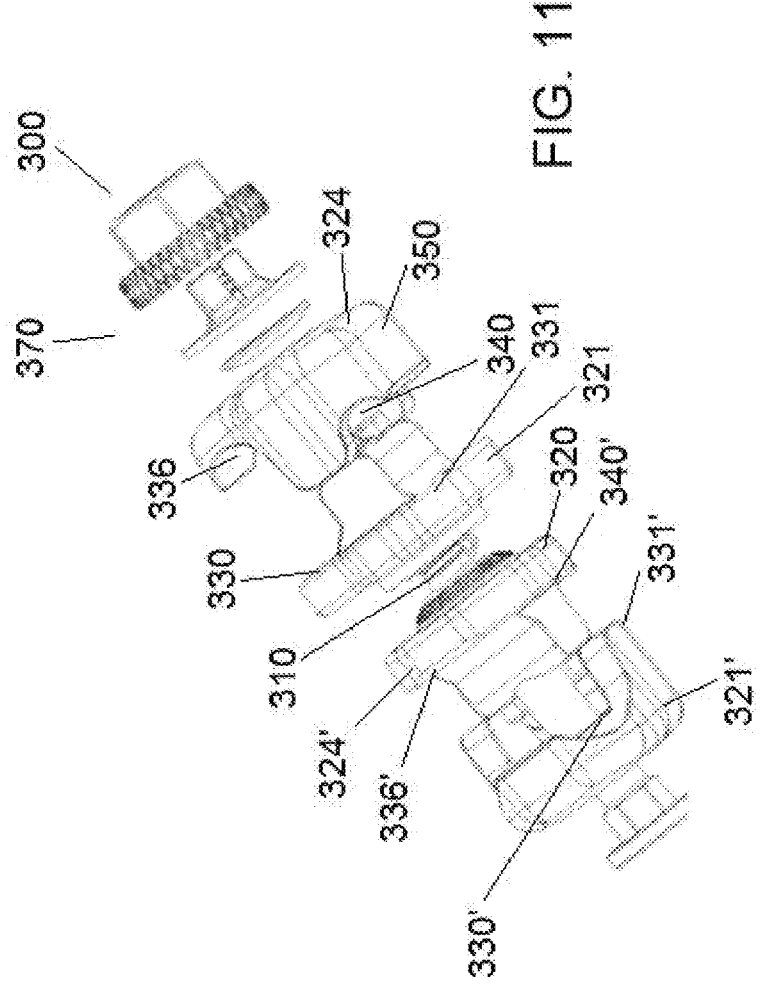
FIG. 11 is a top perspective view of an external fixator assembly according to a third exemplary embodiment being used to fixate adjacent bones.

FIG. 11 is a top perspective view of an external fixator assembly according to a third exemplary embodiment being used to fixate adjacent bones. The external fixator assembly 300 comprises similar features as in prior embodiments, including a first clamp assembly 320, a second clamp assembly 350, a ratchet assembly 370, and a shaft 310 extending through each of the components. The first clamp assembly 320 comprises an upper member 324' operably attached to a lower member 321', thereby forming a pair of slots for receiving one or more pins or rods. Likewise, the second clamp assembly 350 comprises an upper member 324 operably attached to a lower member 321, thereby forming a pair of slots for receiving one or more pins or rods. However, in the present embodiment, at least one of the slots for receiving the one or more pins or rods is formed by one or more flat surfaces (shown in FIG. 12). By providing such flat surfaces, this advantageously provides a distinctly shaped slot that eases both insertion and removal of any pin or rod that is inserted within the slot.

In some embodiments, the first clamp assembly 320 comprises an upper member 324' having a first downward facing recessed portion 336' and a second downward facing recessed portion 340'. In some embodiments, the first downward facing recessed portion 336' and the second downward facing recessed portion 340' are U-shaped or V-shaped. In addition, the first clamp assembly 320 further comprises a lower member 321' having a first upward facing recessed portion 330' and a second upward facing recessed portion 331'. In some embodiments, the first upward facing recessed portion 330' and the second upward facing recessed portion 331' are U-shaped or V-shaped. In some embodiments, the first downward facing recessed portion 336' faces the first upward facing recessed portion 330', thereby forming a first slot in the first clamp assembly for receiving a rod or pin. In some embodiments, the second downward facing recessed portion 340' faces the second upward facing recessed portion 331', thereby forming a second slot in the first clamp assembly for receiving a rod or pin. In some embodiments, the first slot and the second slot in the first clamp assembly 320 are the same size. In other embodiments, the first slot and the second slot in the first clamp assembly 320 are of different sizes.

In some embodiments, the second clamp assembly 350 comprises an upper member 324 having a first downward facing recessed portion 336 and a second downward facing recessed portion 340. In some embodiments, the first downward facing recessed portion 336 and the second downward facing recessed portion 340 are U-shaped or V-shaped. In addition, the second clamp assembly 350 comprises an upward facing flat portion 330 and an upward facing recessed portion 331. In some embodiments, the first downward facing recessed portion 336 faces the first upward facing flat portion 330, thereby forming a first slot in the second clamp assembly for receiving a rod or pin. In some embodiments, the second downward facing recessed portion 340 faces the second upward facing recessed portion 331, thereby forming a second slot in the second clamp assembly for receiving a rod or pin.

FIG. 12 is a close-up view of a clamp assembly of the external fixator assembly of FIG. 11. From this view, one can see how the clamp assembly 350 includes a first slot for receiving a rod or a pin and a second slot for receiving a rod or a pin, wherein the first slot is different from the second slot. The first slot in the clamp assembly 350 is formed by a first downward facing recessed portion 336 which opposes an upward facing flat portion 330, while the second slot in the clamp assembly 350 is formed by a second downward facing recessed portion 340 which opposes an upward facing recessed portion 331. In other words, the first slot is formed by a single arc opposing a flat surface, while the second slot is formed by opposing double arcs.

As shown in FIG. 12, the first slot further includes flat surfaces 332, 334 that extend between the flat portion 330 and the recessed portion 336, thereby connecting the portions to form the first slot. By providing a first slot with the flat surfaces, this advantageously creates a slot whereby a rod or pin can be easily inserted, but also easily removed from the first slot. As shown in FIG. 12, the second slot is formed by the second downward facing recessed portion 340 transitioning into the upward facing recessed portion 331, thereby forming a slot formed of double arcs.

FIG. 13 is a top perspective view of an external fixator assembly according to a fourth exemplary embodiment being used to fixate adjacent bones. The external fixator assembly 400 comprises similar features as in prior embodiments, including a first clamp assembly 420, a second clamp assembly 450, a ratchet assembly 470, and a shaft 410 extending through each of the components. The first clamp assembly 420 comprises an upper member 424' operably attached to a lower member 421', thereby forming a pair of slots for receiving one or more pins or rods. However, the second clamp assembly 450 comprises an upper member 424 operably attached to a lower member 421, whereby only a single slot is formed for receiving a single rod. As shown in FIG. 13, the single slot is opposed to a rod/pin free zone 433. In other words, the external fixator 400 including the first clamp assembly 420 and the second clamp assembly 450 includes a total of three slots for receiving one or more pins or rods. By providing a second clamp assembly 450 having a single slot for receiving a rod, this advantageously provides a more simplistic connection mechanism and reduces the risk of confusion to a surgeon during surgery.

FIG. 14 is a close-up view of a pair of clamp assemblies of the external fixator assembly of FIG. 13. From this view, one can see how the clamp assembly 450 includes a first slot for receiving a rod that is opposed to a rod/pin free zone 433. The first slot in the clamp assembly 450 is formed by a first downward facing recessed portion 436 which opposes a first upward facing recessed portion 430. The rod/pin free zone 433 is formed of two flat surfaces 437, 439 forming a V-opening relative to one another. The two flat surfaces 437, 439 are sized and shaped such that neither a rod nor pin will not be retained (or in some cases, received) in the recess formed therebetween.

In contrast to the clamp assembly 450, the clamp assembly 420 includes two opposing slots for receiving one or more rods and/or pins. The first slot is formed of a first downward facing recessed portion 436' which opposes a first upward facing recessed portion 430', while the second slot is formed of a second downward facing recessed portion 440' which opposes a second upward facing recessed portion 431'. As shown in FIG. 14, the first slot for receiving a rod is larger than the second slot for receiving a pin.

FIG. 15 is a front view of an interface between a first clamp assembly and a second clamp assembly in accordance with some embodiments. The first clamp assembly 120 comprises an upwardly extending toothed locking half 148, while the second clamp assembly 150 comprises a downwardly extending toothed locking half. In some embodiments, the first clamp assembly 120 comprises an upwardly extending toothed locking half 148 in the form of a female mating feature, while the second clamp assembly 150 comprises a downwardly extending toothed locking half 148 in the form of a male mating feature that is received in the female mating feature. In some embodiments, both the downwardly extending toothed locking half 148 and the upwardly extending toothed locking half comprise grooves in the form of a beveled star grind. When both of the locking halves 148 are engaged with one another, the beveled star grinds engage one another, thereby preventing relative rotation between the first clamp assembly 120 and the second clamp assembly 150. In addition, advantageously the elevated and indented portions of the male and female mating features also allow for the grooves of the star grinds to self-align once tightened. Once the first clamp assembly 120 and the second clamp assembly 150 are tightened, the beveled star grinds are completely enclosed and not visible externally (as shown in FIG. 18). The beveled star grinds disclosed herein can be used with any of the embodiments above of external fixators.

FIG. 16 shows a cross-sectional view of the first clamp assembly and the second clamp assembly of FIG. 15. From this view, one can see how the second clamp assembly 150 includes a toothed locking half 148 in the form of an internal beveled star grind. The beveled star grind of the second clamp assembly 150 engages the beveled star grind of the first clamp assembly 120, as noted above.

FIG. 17 is a close-up view of teeth of a toothed locking half in accordance with some embodiments. The teeth 147 of the toothed locking half 148 are arranged concentrically around an opening for receiving a shaft (e.g., shaft 110) of the clamp assembly 150, thereby forming a beveled star grind. In some embodiments, the teeth 147 are formed continuously around the opening, while in other embodiments, the teeth 147 are formed intermittently around the opening.

FIG. 18 is a close-up view of a first clamp assembly and a second clamp assembly in a fully tightened construct in accordance with some embodiments. In the fully tightened construct, the first clamp assembly 120 and the second clamp assembly 150 are engaged with one another such that their star grind components are not visible. Advantageously, the beveled star grinds will allow for the clamp assemblies to resist rotation relative to one another. In addition, they will also provide a strong consistent hold each time the clamp assemblies are tightened.

Figure 19:
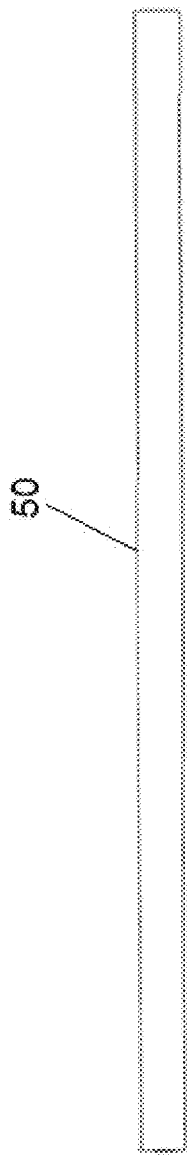
FIG. 19 is a side view of a rod in accordance with some embodiments.

FIG. 19 is a side view of a rod to be used with any of the external fixators above in accordance with some embodiments. The rod 50 can be formed of a biocompatible material. In some embodiments, the rod 50 is formed of carbon fiber. In some embodiments, the rod 50 can be coated with an additional material to make it more compatible for MRI use.

FIG. 20 is a side view of a pin to be used with any of the external fixators above in accordance with some embodiments. The pin 60 can be comprised of a proximal portion 61 and a distal portion 62. The proximal portion 61 can comprise one or more grooves or features that allow for quick connection to a hand-held tool. In some embodiments, the proximal portion 61 comprises an AO quick connect adapter. The distal portion 62 can comprise one or more threads that can be inserted into bone. In some embodiments, two or more pins will be used with any of the external fixators described above. The pins that can be self-tapping and/or self-tapping/self-drilling pins. In some embodiments, the pins can advantageously have a hydroxyl apatite coating in order to prevent pin tract infection. The length and diameter of the pins can vary depending on the patients and surgeon preference. In some embodiments, a pin is provided that can have grooves cut along its shank such that if the end of the pin is cut off, removal can still be easily achieved with another instrument (e.g., a keyless chuck). One skilled in the art that different types of pins can be used with any of the external fixators described above. For example, in some embodiments, two pins can be used with an external fixator whereby the first pin has an AO quick connect adapter, while the second pin does not have an AO quick connect adapter.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. An external fixator assembly comprising:
   a first clamp assembly and a second clamp assembly;
   a shaft extending through the first clamp assembly and the second clamp assembly;
   a ratchet assembly operably attached to the shaft, the ratchet assembly including a buttress member and a housing member, wherein the buttress member includes a tang extending from the buttress member and into a corresponding slot formed in the housing member to prevent relative rotation of the housing member with respect to the buttress member; and
   a plurality of pins retained by the first clamp assembly or the second clamp assembly or a plurality of rods retained by the first clamp assembly or the second clamp assembly,
   wherein the first and second clamp assemblies are configured to rotate relative to one another when the external fixator assembly is in an unlocked position.

2. The external fixator assembly of claim 1, further comprising a spring extending around the shaft.

3. The external fixator assembly of claim 1, wherein the first clamp assembly includes a first slot for receiving one of the plurality of pins or rods and a second slot for receiving one of the plurality of pins or rods, wherein the first slot is different from the second slot.

4. The external fixator assembly of claim 1, wherein when moved to a locked position, the first and second clamp assemblies are fixed in position and are no longer able to rotate relative to one another.

5. The external fixator assembly of claim 4, wherein the first clamp assembly includes an upwardly extending toothed locking half and the second clamp assembly includes a downwardly extending toothed locking half.

6. The external fixator assembly of claim 5, wherein the upwardly extending toothed locking half comprises a first star grind and the downwardly extending toothed locking half comprises a second star grind.

7. The external fixator assembly of claim 6, wherein the first star grind and the second star grind are engaged with one another.

8. The external fixator assembly of claim 7, wherein at least one of the first star grind and the second star grind are beveled.

9. The external fixator assembly of claim 8, wherein when the beveled star grinds engage one another, relative rotation between the first clamp assembly and the second clamp assembly is prevented.

10. The external fixator assembly of claim 1, wherein first or second clamp assembly includes a pin or rod free zone such that a pin or rod would not be retained therein.

11. An external fixator assembly comprising:
a first clamp assembly and a second clamp assembly;
a shaft extending through the first clamp assembly and the second clamp assembly;
a ratchet assembly operably attached to the shaft, the ratchet assembly including a buttress member and a housing member, wherein the buttress member includes a tang extending from the buttress member and into a corresponding slot formed in the housing member to prevent relative rotation of the housing member with respect to the buttress member;
at least one pin retained by the first clamp assembly or the second clamp assembly; and
at least one rod retained by the first clamp assembly or the second clamp assembly.

12. The external fixator assembly of claim 11, further comprising a spring extending around the shaft.

13. The external fixator assembly of claim 11, wherein the first clamp assembly includes a first slot for receiving one of the plurality of pins or rods and a second slot for receiving one of the plurality of pins or rods, wherein the first slot is different from the second slot.

14. The external fixator assembly of claim 11, wherein when moved to a locked position, the first and second clamp assemblies are fixed in position and are no longer able to rotate relative to one another.

15. The external fixator assembly of claim 14, wherein the first clamp assembly includes an upwardly extending toothed locking half and the second clamp assembly includes a downwardly extending toothed locking half.

16. The external fixator assembly of claim 15, wherein the upwardly extending toothed locking half comprises a first star grind and the downwardly extending toothed locking half comprises a second star grind.

17. The external fixator assembly of claim 16, wherein the first star grind and the second star grind are engaged with one another.

18. The external fixator assembly of claim 17, wherein at least one of the first star grind and the second star grind are beveled.

19. The external fixator assembly of claim 18, wherein when the beveled star grinds engage one another, relative rotation between the first clamp assembly and the second clamp assembly is prevented.

20. The external fixator assembly of claim 11, wherein first or second clamp assembly includes a pin or rod free zone such that a pin or rod would not be retained therein.

* * * * *